(12) United States Patent
Kanamori

(10) Patent No.: US 9,645,074 B2
(45) Date of Patent: *May 9, 2017

(54) IMAGE PROCESSING APPARATUS

(71) Applicant: Panasonic Intellectual Property Management Co., Ltd., Osaka (JP)

(72) Inventor: Katsuhiro Kanamori, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 245 days.

This patent is subject to a terminal disclaimer.

(21) Appl. No.: 14/604,858

(22) Filed: Jan. 26, 2015

(65) Prior Publication Data

US 2015/0219552 A1  Aug. 6, 2015

(30) Foreign Application Priority Data

Feb. 6, 2014  (JP) ................. 2014-021032

(51) Int. Cl.
*G01J 4/00* (2006.01)
*G01N 21/21* (2006.01)
*G02B 21/36* (2006.01)
*G01N 21/17* (2006.01)

(52) U.S. Cl.
CPC ........... *G01N 21/21* (2013.01); *G02B 21/365* (2013.01); *G01N 2021/1765* (2013.01); *G01N 2021/216* (2013.01)

(58) Field of Classification Search
CPC ................. G01N 21/21; G01N 21/365; G01N 2021/1765; G01N 2021/216
USPC ......................................................... 356/369
See application file for complete search history.

(56) References Cited

U.S. PATENT DOCUMENTS

| 9,307,159 B2 * | 4/2016 | Kanamori ............ H04N 5/2354 |
| 2003/0040668 A1 | 2/2003 | Kaneko et al. |
| 2010/0253820 A1 | 10/2010 | Kanamori et al. |
| 2014/0303853 A1 | 10/2014 | Itoh et al. |

FOREIGN PATENT DOCUMENTS

| JP | 2003-047588 | 2/2003 |
| JP | 2010-104424 | 5/2010 |
| JP | 2011-098987 | 5/2011 |
| JP | 2013-117519 | 6/2013 |
| WO | 2009/072260 | 6/2009 |

* cited by examiner

*Primary Examiner* — Hina F Ayub
(74) *Attorney, Agent, or Firm* — Wenderoth, Lind & Ponack, L.L.P.

(57) ABSTRACT

An image processing apparatus includes an illumination unit in which illumination axes of first and second illumination light substantially coincide with an imaging axis and which illuminates an object with the first and second illumination light alternately, the first and second illumination light being respectively polarized in a first direction and a second direction that crosses the first direction; a splitter that divides returning light into at least two returning light components; and first and second polarization imaging devices that receive the returning light components. The first polarization imaging device obtains first and second polarization images polarized in the first direction while the object is being illuminated with the first and second illumination light, respectively. The second polarization imaging device obtains third and fourth polarization images polarized in the second direction while the object is being illuminated with the first and second illumination light, respectively.

22 Claims, 29 Drawing Sheets

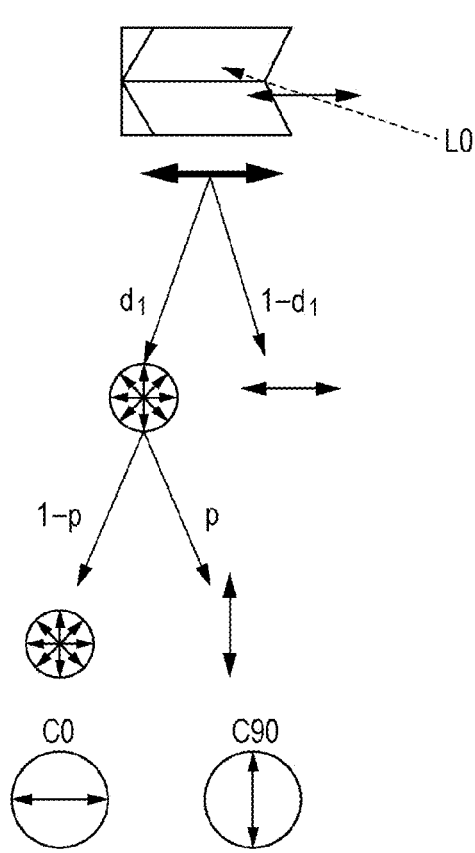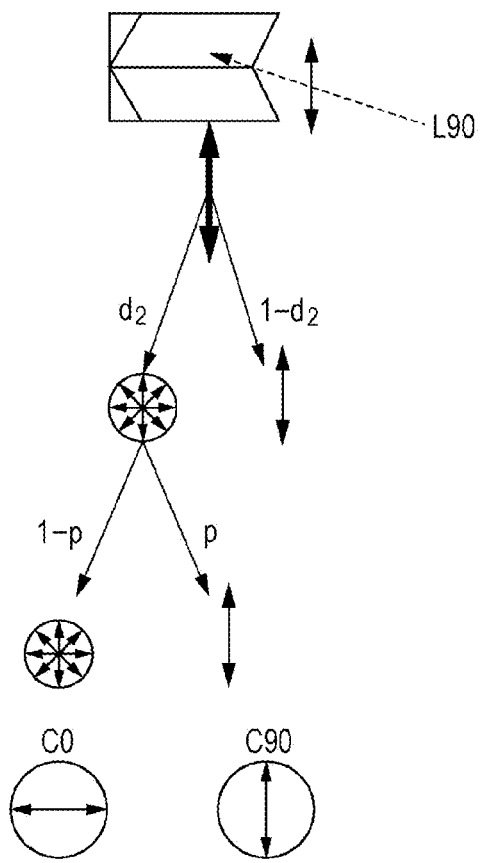

| 0.000229 | 0.003312 | 0.008064 | 0.003312 | 0.000229 |
| 0.003312 | 0.047809 | 0.116411 | 0.047809 | 0.003312 |
| 0.008064 | 0.116411 | 0.283456 | 0.116411 | 0.008064 |
| 0.003312 | 0.047809 | 0.116411 | 0.047809 | 0.003312 |
| 0.000229 | 0.003312 | 0.008064 | 0.003312 | 0.000229 |

FIG. 14
(1) $\Delta C \leq C1$   (2) $C1 < \Delta C \leq (C1+C2)/2$   (3) $(C1+C2)/2 < \Delta C$
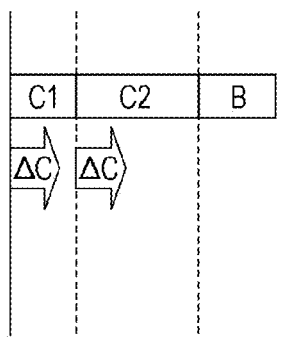
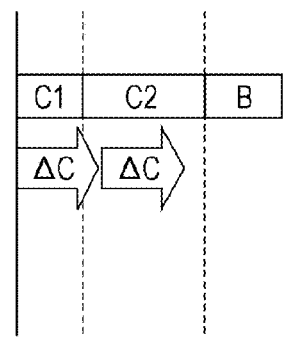
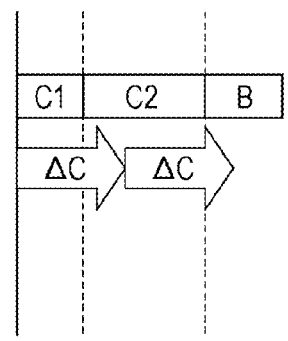

FIG. 23
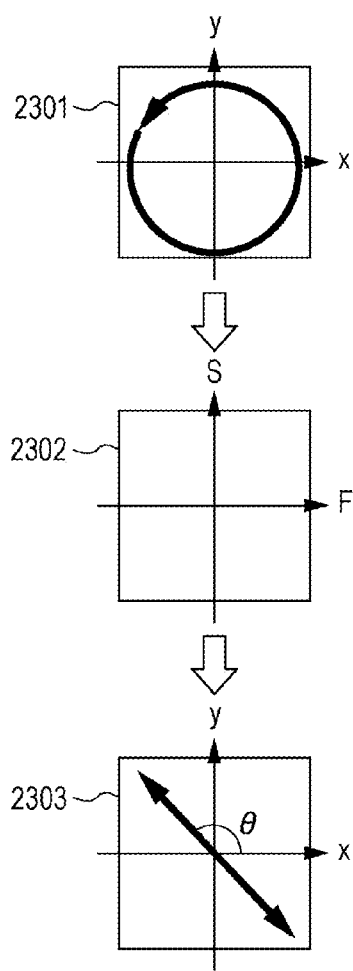
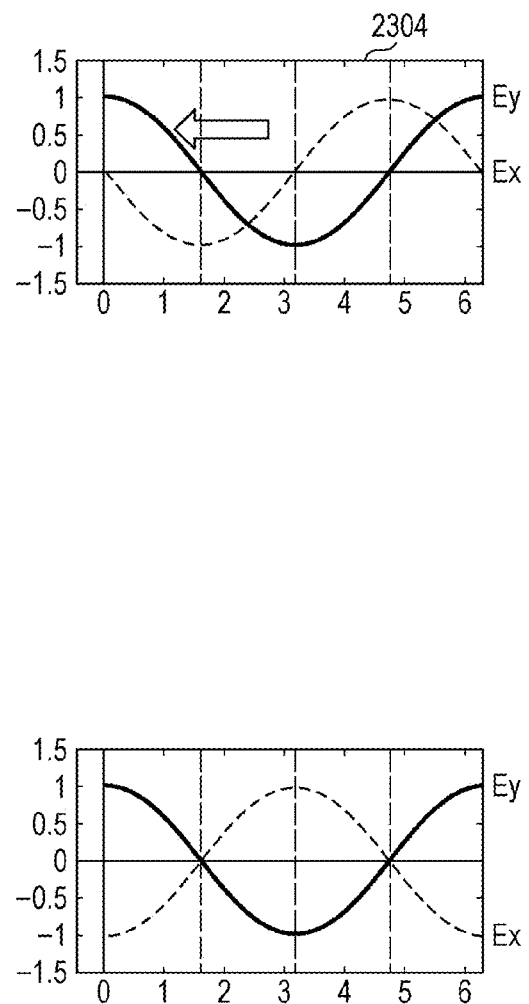

FIG. 24
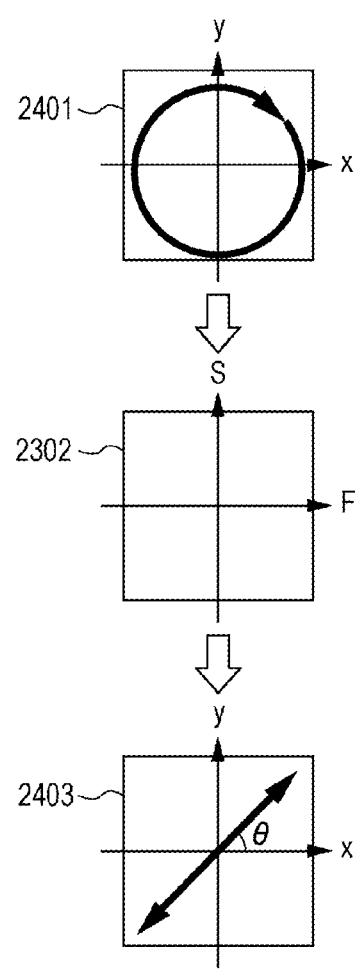
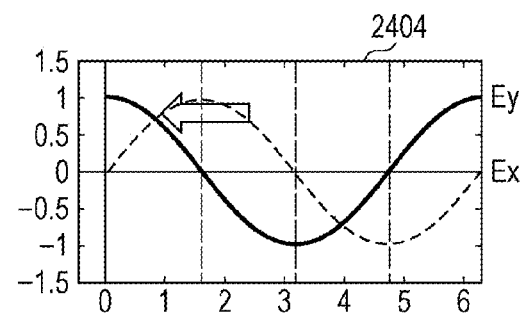
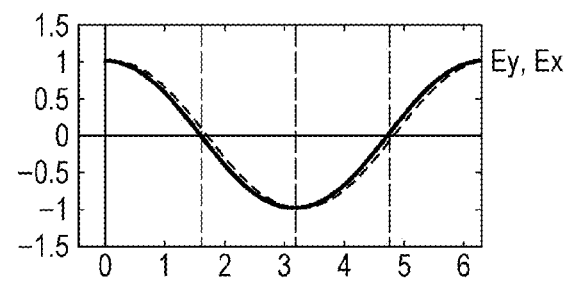

FIG. 28
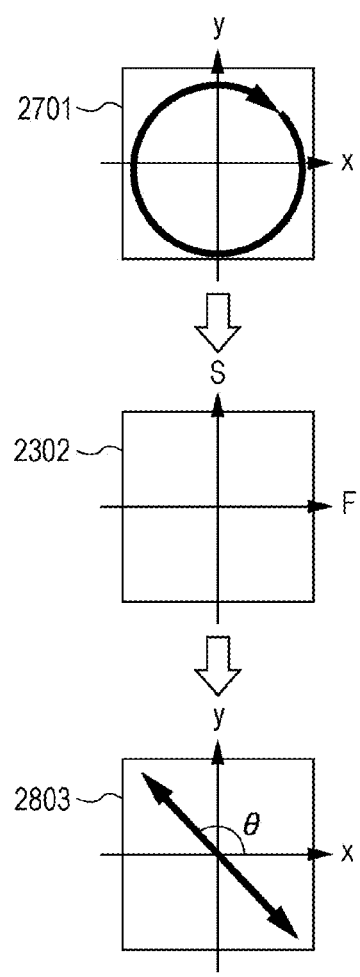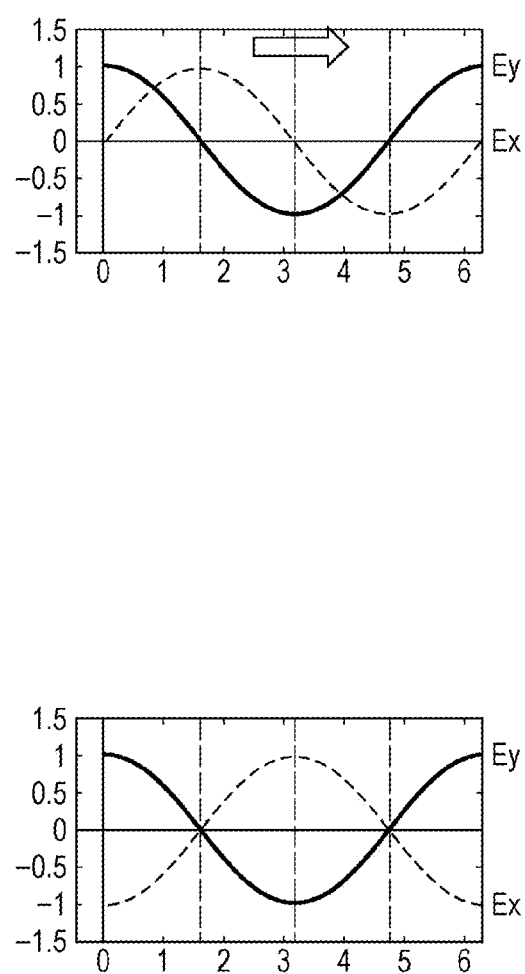

IMAGE PROCESSING APPARATUS

CROSS REFERENCES TO RELATED APPLICATIONS

This application claims priority to Japanese Patent Application No. 2014-021032, filed on Feb. 6, 2014, the contents of which are hereby incorporated by reference.

BACKGROUND

Technical Field

In the field of endoscopes which capture an image of a wall surface of a living organ covered with a mucous membrane by illuminating the wall surface with light, it is necessary to inspect not only a change in the color of the surface but also the texture of small irregularities on the surface. With regard to the surface texture, translucent small irregularities, such as gastric areas, having an average size of about 0.5 to 1.0 mm and a depth of about 0.1 to 0.2 mm are to be inspected. Since it is very difficult to detect them as dark areas with an endoscope, blue pigment liquid such as indigo carmine solution is sprayed on the mucous membrane, and the manner in which the liquid fills grooves is observed in terms of brightness.

However, with this process, since the liquid is sprayed on the mucous membrane, there are risks of bleeding and discoloration of the mucous membrane. For the purpose of observing the irregularities on the surface, polarization illumination and polarization imaging are effective. An endoscope using polarized light has been proposed in Japanese Patent No. 5259033.

SUMMARY

In the endoscope according to the related art disclosed in Japanese Patent No. 5259033, an object is illuminated with a single type of linearly polarized light with fixed polarization. An optical path of returning light that returns from the object is divided into two paths with a prism or the like. Then, an image of a polarized component whose polarization direction is parallel to that of the polarized illumination light and an image of a polarized component whose polarization direction is orthogonal to that of the polarized illumination light are captured in parallel. The captured images are used to visualize a change in the state of polarization in the mucous membrane, which cannot be visualized by brightness imaging. This contributes to early detection of a lesion such as cancer.

A polarization difference process, in which the above-described two types of images are captured in parallel and the difference between the images is determined, has been commonly performed. In this process, it is assumed that the two imaging systems have the same image capturing characteristics.

However, with the technology for performing two types of polarization imaging processes in parallel, it is difficult to completely eliminate the individual differences between the characteristics of imaging devices and the differences in optical characteristics between the optical paths.

One non-limiting and exemplary embodiment provides an image processing apparatus with which it is not necessary to eliminate the individual differences between the characteristics of imaging devices and the differences in optical characteristics between the optical paths.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

In one general aspect, the techniques disclosed here feature an image processing apparatus including an illumination unit that illuminates an object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the image processing apparatus; a splitter that splits returning light that returns from the object into at least two returning light components; a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

With the image processing apparatus according to the present disclosure, the polarized illumination light is switched or the polarization characteristics of the returning light is temporally switched. In addition, every time the polarized illumination light is switched or the polarization characteristics of the returning light is temporally switched, polarization imaging is performed by a plurality of polarization imaging devices. With the image processing apparatus according to the present disclosure, the trouble of matching the characteristics of the plurality of imaging systems can be eliminated, and both a polarization difference image and a non-polarization image can be obtained.

BRIEF DESCRIPTION OF THE DRAWINGS

FIGS. 4A and 4B illustrate the energy of reflected light when polarized illumination light is incident on grooves in a surface in the cases where the polarization direction of the illumination light is at an angle of 0° and 90°, respectively, with respect to the grooves;

FIG. 14 illustrates blue-component emphasizing processes performed in respective cases;

FIG. 23 illustrates the manner in which counterclockwise circularly polarized returning light is converted into linearly polarized light;

FIG. 24 illustrates the manner in which clockwise circularly polarized returning light is converted into linearly polarized light;

FIG. 28 illustrates the manner in which clockwise circularly polarized returning light is converted into linearly polarized light that is polarized in a direction of 135°.

DETAILED DESCRIPTION

Figure 1A:
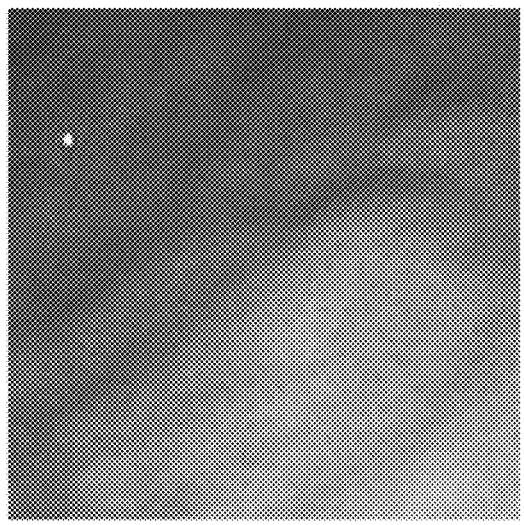
FIGS. 1A and 1B are endoscope images of a gastric mucous membrane.

First, various aspects of the present disclosure will be described.

An image processing apparatus according to an aspect of the present disclosure includes an illumination unit that illuminates an object with the first illumination light and the second illumination light alternately, first illumination light being polarized in a first direction and second illumination light being polarized in a second direction that crosses the first direction, an illumination axis of the first illumination light and an illumination axis of the second illumination light substantially coinciding with an imaging axis of the image processing apparatus; a splitter that splits returning light that returns from the object into at least two returning light components; a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

The processing unit may perform a first process of taking an average of the first polarization image and the fourth polarization image to generate an average parallel-Nicols image; a second process of taking an average of the second polarization image and the third polarization image to generate an average crossed-Nicols image; and a third process of determining the difference by performing a subtraction between the average parallel-Nicols image and the average crossed-Nicols image.

The processing unit may generate a brightness image by adding the first, second, third, and fourth polarization images.

The illumination unit may include a plurality of the first light sources that emit the first illumination light and a plurality of the second light sources that emit the second illumination light.

The image processing apparatus may include an endoscope including an end portion which includes the illumination unit, the splitter, and the first and second polarization imaging devices. The processing unit may be connected to the endoscope.

The image processing apparatus may include an endoscope including an end portion which includes the illumination unit, a polarization camera unit that is disposed behind the end portion, and a relay lens that receives the returning light from the end portion and guides the returning light to the polarization camera unit. The polarization camera unit may include the splitter and the first and second polarization imaging devices, the splitter being arranged so as to receive the returning light guided by the relay lens. The processing unit may be connected to the endoscope.

The processing unit may include a groove-region detecting unit that detects a small groove in a surface of the object.

The processing unit may include an image combining unit which displays the small groove in the surface of the object in an emphasized manner.

The image processing apparatus may further include a minimization process unit that compares a brightness of a pixel of the second polarization image with a brightness of a pixel of the third polarization image corresponding to the pixel of the second polarization image, and selects the pixel having the lower brightness; and an image selecting unit that generates a crossed-Nicols image in which halation is suppressed on the basis of the brightness of the pixel selected by the minimization process.

An image processing apparatus according to another aspect of the present disclosure includes an illumination unit that illuminates an object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the image processing apparatus; a splitter that splits returning light that returns from the object into first, second, and third light components; a first polarization imaging device that receives the first light component, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives the second light component, the second polarization imaging device obtaining a third polarization image polarized in the second direction while the object is being illuminated with the first illumination light and obtaining a fourth polarization image polarized in the second direction while the object is being illuminated with the second illumination light; a third polarization imaging device that receives the third light component, the third polarization imaging device obtaining a fifth polarization image polarized in a third direction, which differs from the first and second directions, while the object is being illuminated with the first illumination light and obtaining a sixth polarization image polarized in the third direction while the object is being illuminated with the second illumination light; and a processing unit that receives the second, third, fifth, and sixth polarization images from the first, second, and third polarization imaging devices and detects a condition of the object on the basis of a difference between a sum of the fifth polarization image and the sixth polarization image and a sum of the second polarization image and the third polarization image.

The first direction and the second direction may be orthogonal to each other, and the third direction may be at an angle in the range of 10 degrees or more and 60 degrees or less with respect to the first direction.

The processing unit may perform a first process of taking an average of the fifth polarization image and the sixth polarization image to generate an average oblique-Nicols image; a second process of taking an average of the second polarization image and the third polarization image to generate an average crossed-Nicols image; and a third process of determining the difference by performing a subtraction between the average oblique-Nicols image and the average crossed-Nicols image.

The processing unit may generate a brightness image by adding the first, second, third, and fourth polarization images.

The illumination unit may include a plurality of the first light sources that emit the first illumination light and a plurality of the second light sources that emit the second illumination light.

The image processing apparatus may include an endoscope including an end portion which includes the illumination unit, the splitter, and the first and second polarization imaging devices. The processing unit may be connected to the endoscope.

The image processing apparatus may include an endoscope including an end portion which includes the illumination unit, a polarization camera unit that is disposed behind the end portion, and a relay lens that receives the returning light from the end portion and guides the returning light to the polarization camera unit. The polarization camera unit may include the splitter and the first and second polarization imaging devices, the splitter being arranged so as to receive the returning light guided by the relay lens. The processing unit may be connected to the endoscope.

The processing unit may include a groove region detecting unit that detects a small groove in a surface of the object.

The processing unit may include an image combining unit which displays the small groove in the surface of the object in an emphasized manner.

An image processing apparatus according to another aspect of the present disclosure include an illumination unit that illuminates an object with first illumination light and second illumination light alternately, the first illumination light being in a first state of polarization and the second illumination light being in a second state of polarization that differs from the first state of polarization, an illumination axis of the first illumination light and an illumination axis of the second illumination light substantially coinciding with an imaging axis of the image processing apparatus; a splitter that splits returning light that returns from the object into at least two returning light components; a phase shift element arranged so as to allow the returning light that returns from the object to pass therethrough, the phase shift element converting clockwise polarized light into light polarized in a first direction and counterclockwise polarized light into light polarized in a second direction that is orthogonal to the first direction; a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light; a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

One of the first state of polarization and the second state of polarization may be clockwise circular or elliptical polarization, and the other one of the first state of polarization and the second state of polarization may be counterclockwise circular or elliptical polarization.

The phase shift element may be a quarter wave plate.

An image processing apparatus according to another aspect of the present disclosure may include an illumination unit that illuminates an object with circularly polarized light or elliptically polarized light, an illumination axis of the circularly polarized light or elliptically polarized light substantially coinciding with an imaging axis of the image processing apparatus; a splitter that splits returning light that returns from the object into at least two returning light components; a variable phase shift element arranged so as to allow the returning light that returns from the object to pass therethrough, the variable phase shift element operating in a first mode and a second mode alternately, the returning light being converted into light in a first state of polarization that is polarized in a first direction in the first mode and being converted into light in a second state of polarization that is polarized in a second direction in the second mode, the second direction being orthogonal to the first direction; a first polarization imaging device that receives one of the at least two returning light components, the first polarization imaging device obtaining a first polarization image polarized in the first direction while the variable phase shift element is operating in the first mode and obtaining a second polarization image polarized in the first direction while the variable phase shift element is operating in the second mode; a second polarization imaging device that receives another one of the at least two returning light components, the second polarization imaging device obtaining a third polarization image polarized in the second direction while the variable phase shift element is operating in the first mode and obtaining a fourth polarization image polarized in the second direction while the variable phase shift element is operating in the second mode; and a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

According to the studies conducted by the present inventor, with the apparatus according to the related art, it is difficult to provide an image device with complete elimination of the individual differences between the characteristics and the differences in optical characteristics between optical paths. As a result, the accuracy of a polarization difference image is reduced and there is a risk that a target lesion cannot be detected. When the polarization difference image is subjected to a gain-up (amplification) process, the differences in characteristics increase and the image quality may become intolerable. Furthermore, since only one type of polarized illumination light polarized in a certain direction is used for illumination, when a brightness image is obtained by taking the average of two types of polarization images obtained by parallel and orthogonal imaging systems, the polarization of the returning light is affected by anisotropy, such as tilt or curve of the surface of an organ. As a result, the brightness image based on the two types of polarization images differs from a brightness image based on a non-polarization image obtained by using normal white non-polarized light.

Embodiments of the present disclosure provide an image processing apparatus with which it is not necessary to eliminate the individual differences between the characteristics of imaging devices and the differences in optical characteristics between optical paths.

First, the principle of detection of small groove regions in the surface of an object by polarization imaging described in embodiments of the present disclosure will be described.

Figure 1B:

FIGS. 1A and 1B are images of a surface mucous membrane of a human stomach observed with an endoscope. FIG. 1A is a brightness image that corresponds to a normal color image, and only gentle undulation of the surface can be observed. This shows that, with normal color image processing, it is difficult to detect transparent or translucent irregularities formed on a surface of an organ by using an endoscope for inspecting a digestive organ or the like. Here, normal color image processing is a process for obtaining a color brightness image by illuminating an object with non-polarized white light. The thus-obtained color image is referred to as a "color brightness image" or simply as a "brightness image", and an imaging process for obtaining a color brightness image is referred to as "color brightness imaging".

FIG. 1B shows an image obtained after spraying indigo carmine solution. The texture of small irregularities on the surface having a size of about 0.5 to 1.0 mm and a depth of about 0.1 to 0.2 mm can be clearly observed.

Figure 2:
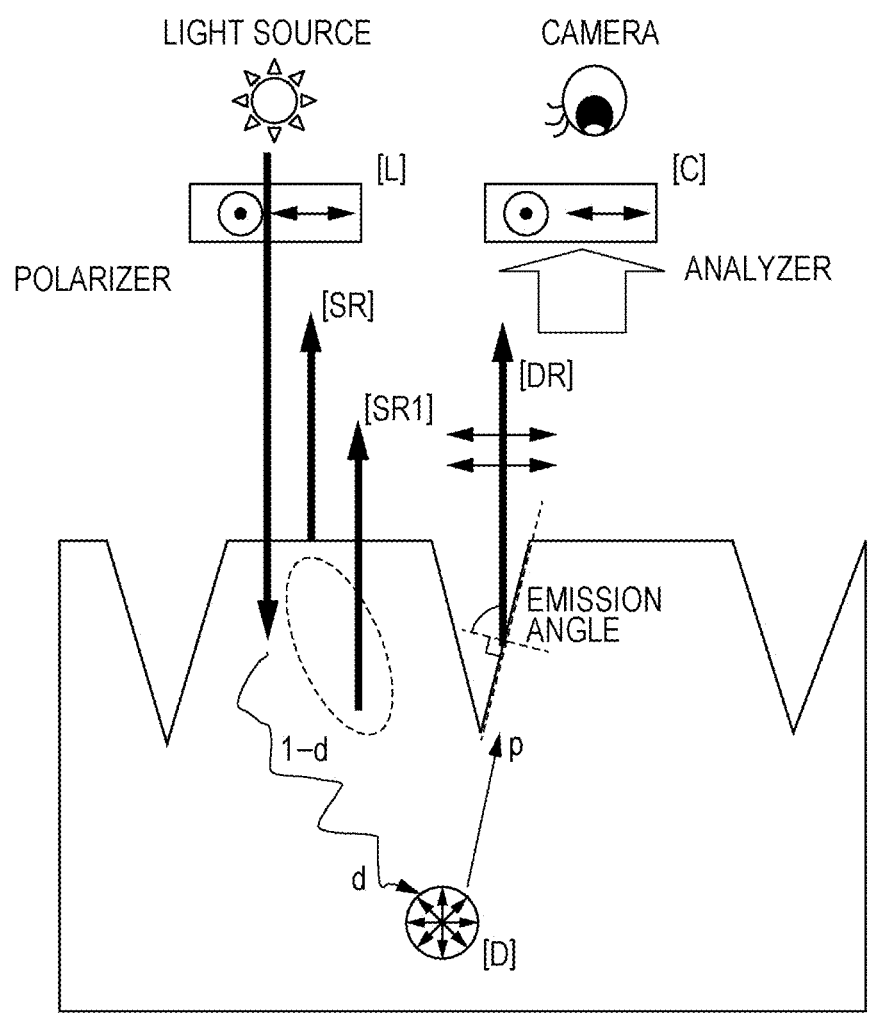
FIG. 2 illustrates a cross-sectional model of an irregular portion on a surface mucous membrane of an organ.

FIG. 2 illustrates a simplified cross-sectional model of irregularities on the surface of an organ such as the stomach or intestine. In general, it is said that grooves in the surface of the stomach or intestine are formed between upward trapezoidal projections that are arranged next to each other. A groove region located between two adjacent projections is typically a small "groove" that extends in a certain direction. Although grooves extend in substantially the same direction in local areas, the grooves may form a complex curved pattern or other patterns in a broader view. In practice, irregularities on an object surface may include dot-shaped recesses or projections. However, in this specification, the recesses included in the irregularities may be referred to simply as "grooves" or "recessed grooves". FIG. 2 illustrates a schematic sectional view of some grooves in a small area of the object surface taken along a plane that crosses the grooves. For simplicity, in the following description, it may be assumed that recesses and projections shown in FIG. 2 extend in a direction perpendicular to FIG. 2.

Observation with an endoscope is performed by coaxial illumination in which a light source is arranged near an imaging axis. Therefore, the object illustrated in FIG. 2 is illuminated with illumination light from directly above the object, and an image thereof is captured at a location directly above the object. There are mainly three types of reflected light that can be observed in normal color brightness imaging in which the above-described coaxial illumination is performed. The first reflected light is mirror reflection light SR that is reflected by the surface (so-called halation). The second reflected light is surface scattering light SR1 which penetrates into a medium and reflected by a surface layer. The third reflected light is inner diffusion light DR which penetrates into a deeper layer of the material as a result of multiple scattering and then re-emitted from the surface. The first reflected light (mirror reflected light) is generated only when the illumination light and the imaging axis substantially satisfy the conditions of regular reflection, and is therefore generated only in local areas in an imaging scene of an endoscope.

The color of the mirror reflection light is the same as that of the illumination light, that is, white, and therefore the mirror reflection light is extremely bright. According to the above-described conditions of regular reflection, the object image obtained by the mirror reflection light is generally strong and bright at projections on the object surface, and dark and dim at grooves in the object surface.

The second type of reflected light (surface scattering light) and the third type of reflected light (inner diffusion light) are observed over the entire area of the imaging scene. The color of these two types of light is the same as that of the medium. The two types of light are not very bright, but are generated over the entire area of the medium.

In a normal imaging process, reflection of the first reflected light (mirror reflection light SR) is often avoided, and the second reflected light and the third reflected light are superposed so as to form a single brightness image (imaging scene).

Referring to FIG. 2, a case in which polarized light is used will be described. In the example illustrated in FIG. 2, illumination light polarized in the extending direction of the projections and recesses on the surface and illumination light polarized in a direction perpendicular to the extending direction are successively emitted. A polarization image in a parallel-Nicols state and a polarization in a crossed-Nicols state are observed for each type of illumination light.

The mirror reflection component SR is regularly reflected in the state of coaxial illumination, and therefore the state of polarization thereof does not change from that of the polarized illumination light. Thus, the state of polarization of the mirror reflection component SR is the same as that of the illumination light.

The surface scattering light SR1 also returns from the surface while the polarization characteristics of the illumination light are maintained. Thus, the polarization characteristics of both the mirror reflection light SR and the surface scattering light SR1 are substantially the same as those of the illumination light. In contrast, the inner diffusion light DR has a different polarization direction. The polarized light that has reached a deep portion of the medium as a result of multiple reflection is converted into non-polarized (randomly polarized) light D due to the influence of multiple reflection. Then, the non-polarized light D is re-emitted from the surface into the air. In a normal flat portion, it is assumed that this light D is emitted as non-polarized light. However, when the surface has grooves, since inclined boundary surfaces are present, the light D is polarized again when the light D is emitted. Polarization that occurs when light is emitted into the air from a medium having a refractive index that is greater than 1 is determined by the Fresnel theory.

Figure 3:
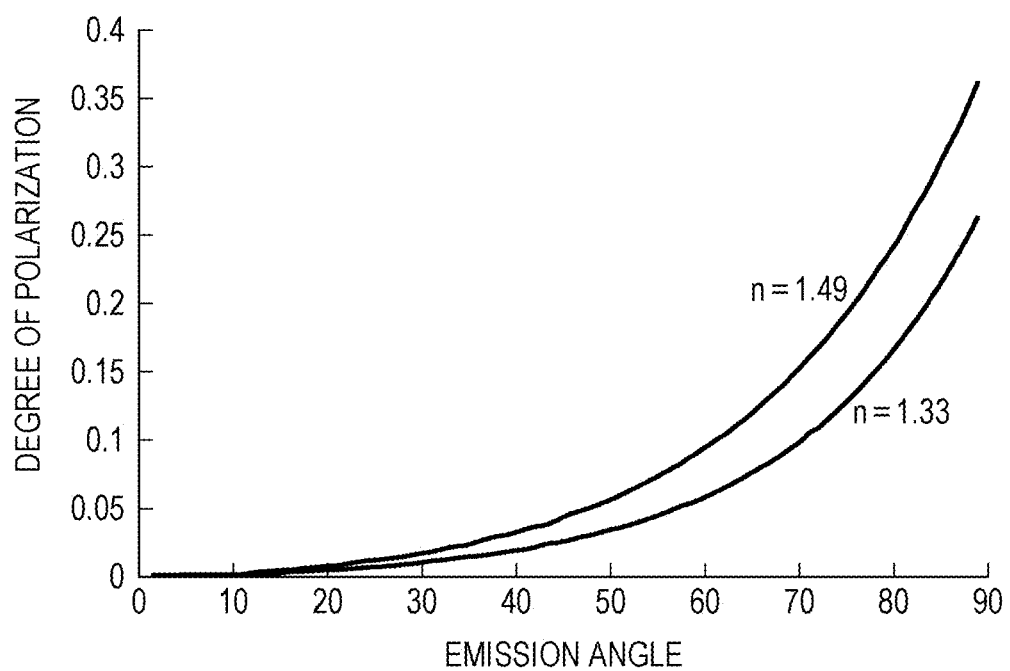
FIG. 3 is a graph showing the relationship between the emission angle at which light is emitted from a medium and the degree of polarization (DOP) based on the Fresnel theory.

FIG. 3 is a graph showing the state of polarization of light when the light is emitted from a medium having a refractive index that is greater than 1, the state of polarization being determined on the basis of the Fresnel theory. Although the degree of polarization is relatively small, it can be understood that the light is polarized such that the transmittance of P-polarized light is always greater than that of S-polarized light at any emission angle on the horizontal axis. When the refractive indices of a living body (water) and an acrylic plate or the like are about 1.33 and 1.49, respectively, the degree of polarization (DOP) is 0.1 (less than 10%) when the emission angle is 70°.

Figure 5:
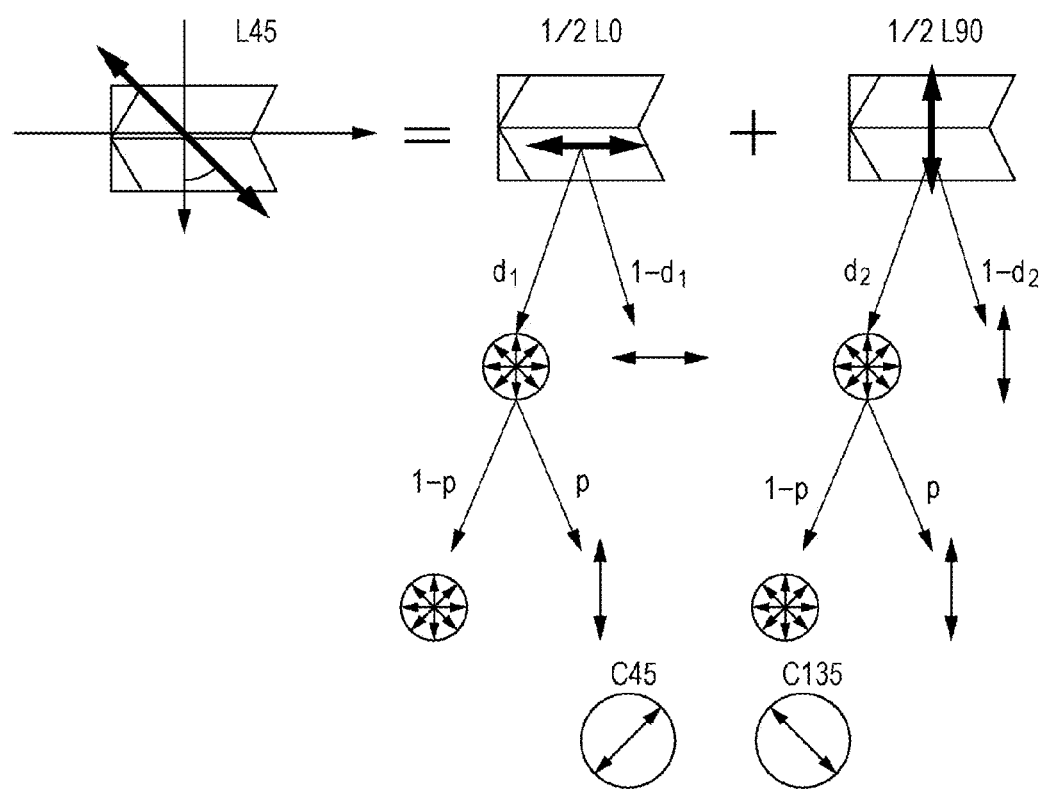
FIG. 5 illustrates the energy of reflected light when polarized illumination light is incident on grooves in a surface in the case where the polarization direction of the illumination light is at an angle of 45° with respect to the grooves.

Here, the brightness contrast in the case where polarization imaging is performed by illuminating the grooves in the surface with polarized illumination light is discussed without taking absorption of the light by the mucous membrane into account. Referring to FIGS. 4A, 4B, and 5, the angle of direction of the grooves is fixed to 0° in a two-dimensional camera coordinate plane, and the grooves are illuminated with three types of light having respective polarization directions, which are denoted by L0, L90, and L45. Here, L0 denotes illumination light with a polarization direction whose angle of direction is 0 degrees, L90 denotes illumination light with a polarization direction whose angle of direction is 90 degrees, and L45 denotes illumination light with a polarization direction whose angle of direction is 45 degrees.

Brightness observation is performed by changing the angle of analyzers disposed in front of a camera in a similar manner (C0, C90, and C45). Here, C0 represents the observation performed by an analyzer with a polarization direction whose angle of direction is 0 degrees, C90 represents the observation performed by an analyzer with a polarization direction whose angle of direction is 90 degrees, and C45 represents the observation performed by an analyzer with a polarization direction whose angle of direction is 45 degrees. The case in which L and C are in a parallel-Nicols state is represented by ∥, and the case in which L and C are in a crossed-Nicols state is represented by ⊥.

L0C0 represents the observation state, the observed brightness, or the observed image in the case where the illumination light with a polarization direction whose angle of direction is 0 degrees is emitted and the analyzer with a polarization direction whose angle of direction is 0 degrees is used.

L0C90 represents the observation state, the observed brightness, or the observed image in the case where the illumination light with a polarization direction whose angle of direction is 0 degrees is emitted and the analyzer with a polarization direction whose angle of direction is 90 degrees is used.

L90C0 represents the observation state, the observed brightness, or the observed image in the case where the illumination light with a polarization direction whose angle of direction is 90 degrees is emitted and the analyzer with a polarization direction whose angle of direction is 0 degrees is used.

L90C90 represents the observation state, the observed brightness, or the observed image in the case where the illumination light with a polarization direction whose angle of direction is 90 degrees is emitted and the analyzer with a polarization direction whose angle of direction is 90 degrees is used.

Thus, LXCY represents the observation state, the observed brightness, or the observed image in the case where illumination light with a polarization direction whose angle of direction is X degrees is emitted and an analyzer with a polarization direction whose angle of direction is Y degrees is used.

(1) L0C0 (∥) and L0C90 (⊥) (FIG. 4A)

When the energy of the incident linearly polarized light is 1 and the ratio of a part of the polarized light that is diffused in the medium and converted into non-polarized light is $d_1$, the ratio of a part of the polarized light that is reflected while the polarization thereof is maintained, as in light SR and SR1, is $(1-d_1)$. Next, it is assumed that the ratio of a part of the non-polarized light in the medium that is converted into linearly polarized light when the light is re-emitted into the air is p, and the ratio of a part of the non-polarized light that remains in the non-polarized state is $(1-p)$. When these reflected light components are observed by C0, that is, by a polarizing plate of 0°, the energy of the parallel linearly polarized light completely passes through the polarizing plate, while the energy of the orthogonal linearly polarized light is reduced to zero. Also, the energy of the non-polarized light is reduced to ½ when observed by with a linear polarizing plate. Therefore, the brightness of the parallel-Nicols (∥) image for L0 can be expressed as follows:

$$L0C0=(1-d_1)+d_1(1-p)/2=1-d_1(1+p)/2 \quad (1)$$

The brightness of the crossed-Nicols (⊥) image for L0 can be expressed as follows:

$$L0C90=d_1p+d_1(1-p)/2=d_1(1+p)/2 \quad (2)$$

(2) L90C90 (∥) and L90C0 (⊥) (FIG. 4B)

When the ratio of a part of the polarized light that is diffused in the medium and converted into non-polarized light is $d_2$, the brightness of the parallel-Nicols (∥) image can be expressed as follows:

$$L90C90=(1-d_2)+d_2p+d_2(1-p)/2=1-d_2(1-p)/2 \quad (3)$$

The brightness of the crossed-Nicols (⊥) image can be expressed as follows:

$$L90C0=d_2(1-p)/2 \quad (4)$$

(3) L45C45 (∥) and L45C135 (⊥) (FIG. 5)

In this case, Equations (1) to (4) may be applied after dividing the polarized light into components of 0° and 90° such that the energy of each component is ½. On the basis of the Malus' law, the brightness of the parallel-Nicols (∥) image can be expressed by using $\cos^2 45°$ as follows:

$$L45C45=\tfrac{1}{2}\times[\cos^2 45°\times\{d_1p+(1-d_1)+d_2p+(1-d_2)\}+d_1/2\times(1-p)+d_2/2\times(1-p)]=\tfrac{1}{2} \quad (5)$$

Similarly, the brightness of the crossed-Nicols (⊥) image can be expressed as follows:

$$L45C135=\tfrac{1}{2} \quad (6)$$

To determine the brightness contrast in polarization difference observation, first, a case in which the above-described polarized light is incident on a flat medium will be considered. Similar to the above-described case, it is assumed that the ratio of a part of the linearly polarized light that is converted into the non-polarized light in the medium is d. In the parallel-Nicols image, contribution by the reflected component in which the polarization is maintained is (1−d) and that by the non-polarized light is d/2, so that the total is 1−d/2. In the crossed-Nicols state, only contribution of d/2 by the non-polarized light component is provided.

Table 1 given below shows the brightness in the groove portions (Groove-region) and the flat portions (Plane-region) in accordance with the polarization angle. Table 1 also shows the polarization difference value (∥−⊥) and the brightness contrast calculated by using the polarization difference value. Here, the brightness contrast is defined as (flat portion brightness (Plane))/(groove portion brightness (Groove)). To simplify the calculation, in the brightness contrast column of Table 1, it is assumed that $d_1=d_2=d$.

TABLE 1

| | Groove-region | | | Plane-region | | Contrast |
| --- | --- | --- | --- | --- | --- | --- |
| | ∥ | ⊥ | ∥ − ⊥ | ∥ | ⊥ | ∥ − ⊥ (Plane/Groove) |
| L0 | 1 − $d_1$(1 + p)/2 | $d_1$(1 + p)/2 | 1 − $d_1$(1 + p) | 1 − d/2 | d/2 | 1 − d/(1 + dp)(1 + p) |
| L90 | 1 − $d_2$(1 − p)/2 | $d_2$(1 − p)/2 | 1 − $d_2$(1 − p) | | | 1 − dp/(1 − d(1 − p)) |
| L45 (L135) | 1/2 | 1/2 | 0 | | | ∞ |

It is clear from Table 1 that, irrespective of the actual values of p and d, the brightness contrast is higher than 1 in the cases of L0 and L45 (L135). Also, when the polarization difference is used, the brightness contrast is the highest and ideally infinite in the case of L45 (L135), that is, when the polarization plane of the polarized illumination light is at an angle of 45° with respect to the grooves, and is the second highest and exceeds 1 in the case of L0, that is, when the polarization plane of the polarized illumination light is parallel to the grooves. The brightness contrast is the lowest and is less than or equal to 1 in the case of L90, that is, when the polarization plane of the polarized illumination light is orthogonal to the grooves.

When it is assumed that the direction of the grooves in the object surface is random and the polarization direction of the illumination light is varied in steps of 45°, the probability that the brightness contrast will be higher than 1 is ¾ (=75%). Here, there is a 25% probability that the contrast will be reduced. However, according to the results of experiments conducted by the present inventor, a detection result that is more satisfactory than that obtained from a normal brightness image can be obtained by emitting two types of polarized illumination light whose polarization directions are 0° and 90°, performing image processing for groove detection, which will be described below, for each of the two types of polarized illumination light, and forming an image by taking the average of the results of image processing. When two types of illumination light whose polarization directions are 45° and 135° are used, a satisfactory result can, of course, be obtained. Thus, when the polarization difference observation is performed by using two types of polarized illumination light having orthogonal polarization directions, the flat portions and the groove portions can be observed at a very high contrast. This is the principle of detection of the groove portions according to the present disclosure.

Next, the brightness contrast in brightness observation according to the related art in which polarized light is not used will be discussed. Here, the brightness contrast between the groove portions and the flat portions in the case where normal non-polarized illumination light NP is used will be discussed. First, the groove portions are considered. When it is assumed that the angle of direction of incidence is φ and the angle of direction of observation is θ, the average of φ of the illumination light for the observation angles P and S is ½. Therefore, the following equation is satisfied for P.

$$L(NP)P(\theta)=$$

$$\tfrac{1}{2}\times[(1-d_1)\cos^2\theta+d_1p\sin^2\theta]$$

$$+\tfrac{1}{2}\times[(d_2p\sin^2\theta+(1-d_2)\sin^2\theta]$$

$$+(1-p)(d_1+d_2)/4 \quad (7)$$

In addition, the following equation is satisfied for S.

$$L(NP)S(\theta+)90°=$$

$$\tfrac{1}{2}\times[(1-d_1)\sin^2\theta+d_1p\cos^2\theta]$$

$$+\tfrac{1}{2}\times[d_2p\cos^2\theta+(1-d_2)\cos^2\theta]$$

$$+(1-p)(d_1+d_2)/4 \quad (8)$$

Since no analyzer is used in the brightness observation, P+S is observed. For the flat portions, the values are the same as those in Table 1 since there is no anisotropy.

The brightness contrast determined from the above-described results is 1, as shown in Table 2. Thus, it is clear that the groove portions and the flat portions cannot be distinguished from each other based on the brightness.

TABLE 2

| Groove-region | | | Plane-region | | | Contrast (Plane/ |
|---|---|---|---|---|---|---|
| P (θ) | S (θ + 90°) | P + S | P (θ) | S (θ + 90°) | P + S | Groove) |
| $1/2 \times [(1 - d_1)\cos^2 \theta + d_1 p \sin^2 \theta] + 1/2 \times [(d_2 p \sin^2 \theta + (1 - d_2) \sin^2 \theta] + (1 - p)(d_1 + d_2)/4$ | $1/2 \times [(1 - d_1)\sin^2 \theta + d_1 p \cos^2 \theta] + 1/2 \times [(d_2 p \cos^2 \theta + (1 - d2) \cos^2 \theta] + (1 - p)(d_1 + d_2)/4$ | 1 | 1 − d/2 | d/2 | 1 | 1 |

By comparing Tables 1 and 2 with each other, in the model of small structures on the surface mucous membrane described above with reference to FIG. 2, the principle of the process for emphasizing the groove portions can be summarized as follows.

(i) It is difficult to distinguish the groove portions and the flat portions from each other by the non-polarized illumination light and brightness observation since the brightness contrast is low.

(ii) The brightness contrast between the groove portions and the flat portions can be greatly increased when the polarization difference value (∥−⊥) is calculated by using the polarized illumination light and performing polarization imaging.

(iii) However, the brightness contrast depends on the angle between the polarization direction of the incident illumination light and the grooves on a plane. The brightness contrast is at a maximum when the angle difference is 45° (L45), at a minimum when the angle difference is 90° (L90), and between the maximum and minimum when the angle difference is 0° (L0).

(iv) When the groove portions are detected by calculating polarization difference values for two types of illumination light having orthogonal polarization directions that differ by 90° degrees and determining the average of the polarization difference values, satisfactory detection results can be obtained without detection failure.

The present inventor conducted an experiment of producing the above-described polarization difference image of a gastric mucous membrane of a pig. As a result, small groove portions having a width of about several millimeters, which were substantially indiscernible in a color brightness image, were darker than the flat portions and clearly visible. Thus, the effect of emphasizing the contrast was confirmed. When the polarization direction of the illumination light was varied between 0° and 90°, the polarization difference image clearly changed for large surface structures, such as surface creases having a size of about 10 mm. However, no direct correlation was observed between the polarization difference image and the extending direction of the small groove portions. This is probably because unlike artificial smooth surfaces, the normal to the inclined surfaces of the small grooves vary and has low correlation with the extending direction of the grooves. With such groove portions, it can be assumed that the angle between the polarization direction of the illumination light and the extending direction of the grooves is random and is 45 degrees on average. Therefore, as is clear from Table 1, the brightness in the groove portions is substantially zero and the contrast is greatly increased.

Next, an example of the basic structure of a non-limiting exemplary embodiment of the present disclosure will be described.

An image processing apparatus according to an aspect of the present invention includes an illumination unit arranged such that an illumination axis substantially coincides with an imaging axis. Here, "substantially coincides" means that the angle between the axes is in the range of 0° to 30°. The illumination unit illuminates an object with first illumination light and second illumination light alternately, the first illumination light being polarized in a first direction and the second illumination light being polarized in a second direction that crosses the first direction. Here, "an illumination axis substantially coincides with an imaging axis" means that "an illumination axis of the first illumination light and an illumination axis of the second illumination light substantially coincide with the imaging axis". The imaging axis is an axis perpendicular to a surface of an imaging device or an objective lens surface in the image processing apparatus. The angle between the first and second directions may be set in the range of, for example, 45° to 135°, and is typically 90° or about 90°. In the present disclosure, the illumination of the object with the first illumination light and the second illumination light "alternately" does not exclude the case in which illumination with another illumination light (third illumination light) is performed between the illuminations with the first illumination light and the illumination with the second illumination light.

The image processing apparatus includes a splitter that splits returning light that returns from the object into at least two returning light components, a first polarization imaging device that receives one of the returning light components, and a second polarization imaging device that receives the other one of the returning light components. The first polarization imaging device obtains a first polarization image (L0C0) polarized in the first direction while the object is being illuminated with the first illumination light, and obtains a second polarization image (L90C0) polarized in the first direction while the object is being illuminated with the second illumination light. The second polarization imaging device obtains a third polarization image (L0C90) polarized in the second direction while the object is being illuminated with the first illumination light, and obtains a fourth polarization image (L90C90) polarized in the second direction while the object is being illuminated with the second illumination light.

The image processing apparatus further includes a processing unit that detects a condition of the object. The processing unit receives the first, second, third, and fourth polarization images from the first and second polarization imaging devices, and detects the condition of the object on the basis of a difference between the sum of the first polarization image (L0C0) and the fourth polarization image (L90C90) and the sum of the second polarization image (L90C0) and the third polarization image (L0C90).

In the above-described example of the image processing apparatus, the illumination unit is configured to illuminate the object with the first illumination light and the second illumination light alternately, the first illumination light being polarized in the first direction and the second illumination light being polarized in the second direction that crosses the first direction. However, as described below, the object may instead be illuminated with circularly or elliptically polarized light in which a component polarized in the first direction and a component polarized in the second direction that crosses the first direction are combined together with a certain phase therebetween. The illumination unit may have various structures, and the structure thereof is not limited to those described in the embodiments described below.

Embodiments of the present disclosure will be described in detail with reference to the drawings. However, unnecessarily detailed descriptions may be omitted. For example, detailed descriptions of well-known items and repetition of descriptions of components having the same structures may omitted to avoid unnecessarily redundant descriptions and facilitate understanding for persons skilled in the art.

The accompanying drawings and the following description are provided to allow persons skilled in the art to fully understand the present disclosure, and are not intended to limit the subject matter described in the claims.

First Embodiment

Figure 6:
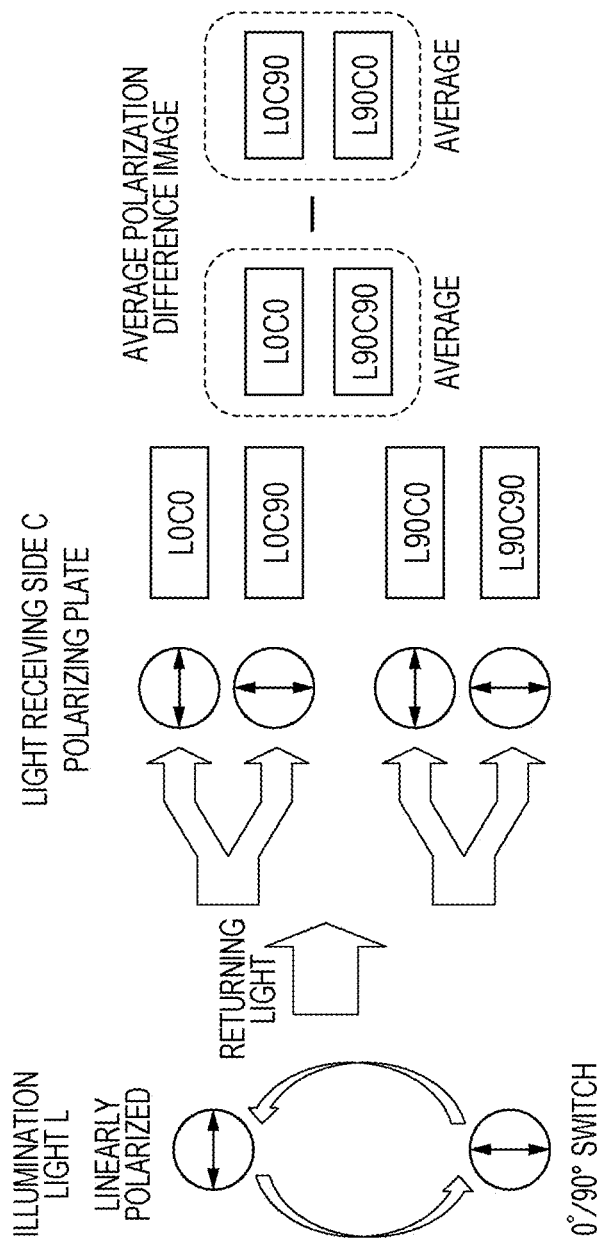
FIG. 6 illustrates a polarization imaging method according to a first embodiment of the present disclosure.

FIG. 6 illustrates the procedure of an image processing method according to a first embodiment of the present disclosure.

An object is illuminated with illumination light L, which is linearly polarized light having an electric field oscillation plane at a polarization angle that is temporally alternately switched between 0° (horizontal) and 90° (vertical) on a plane perpendicular to the travelling direction of the light. For simplicity, in the following description, the state of polarization in which the electric field oscillation plane is at a polarization angle of 0° (horizontal) on the plane perpendicular to the travelling direction of the light may be referred to as "0°", and the state of polarization in which the electric field oscillation plane is at a polarization angle of 90° (vertical) on the plane perpendicular to the travelling direction of the light may be referred to as "90°". A receiving camera C receives returning light, divides the returning light into two light components, and performs two types of polarization imaging processes in parallel by using linear polarizing filters having polarization transmission axes in the directions of 0° (horizontal) and 90° (vertical) on a plane, similar to the illumination light. Thus, when the state of polarization of the illumination light L is 0°, a parallel-Nicols image L0C0 and a crossed-Nicols image L0C90 are obtained. When the state of polarization of the illumination light L is 90°, a crossed-Nicols image L90C0 and a parallel-Nicols image L90C90 are obtained.

According to the related art, in this case, two polarization images are captured by using two light components into which the returning light is divided while the state of polarization of the linearly polarized illumination light L is fixed to 0° or 90°. Since the two polarization images are captured by two imaging systems having different imaging characteristics, when a polarization difference image is obtained by determining the difference between the two images, the obtained image includes the difference in imaging characteristics. According to the related art, the only way to address this problem is to perform a calibration through image processing. However, since the polarization difference image is subjected to a gain-up (amplification) operation for gradation correction in the following step of image processing, reduction in image quality and precision cannot be avoided.

In contrast, according to the present embodiment, the above-described problem is solved by generating an average polarization difference image by using four images in total, the four images being obtained by switching the polarization direction of the illumination light L. When the polarization direction of the illumination light L is switched, the roles of the two imaging systems of the camera C switch between parallel-Nicols and crossed-Nicols. Therefore, the averages of the images obtained by the two different imaging systems can be determined. More specifically, images Iav, which include an average parallel-Nicols image Iav(∥) and an average crossed-Nicols image Iav(⊥), can be generated as images captured by a virtual imaging system having intermediate characteristics between the characteristics of the two different imaging systems.

$$Iav(\|)=[L0C0+L90C90]/2$$

$$Iav(\perp)=[L0C90+L90C0]/2 \qquad (9)$$

An average polarization difference image Idif is calculated from the images Iav.

$$Idif=Iav(\|)-Iav(\perp) \qquad (10)$$

In the thus-generated average polarization difference image, the difference between the characteristics of the two imaging systems is canceled. Therefore, satisfactory image quality can be maintained even when the gain-up process or the like is performed in the following step of image processing.

In this specification, "average" means that pixel values of a plurality of images are added in units of pixels, and it is not necessary to divide the sum by the number of images. In the example of Equations (9), the sum is divided by 2, which is the number of images. However, it is not necessary to divide the sum by 2.

In the above-described examples of Equations (9) and (10), the difference is calculated after the averages are determined. However, differences may be calculated first, and then the average of the differences may be determined. More specifically, the average of the difference "L0C0−L0C90" and the difference "L90C0−L90C90" may be determined by adding the differences.

Thus, according to the present embodiment, the first, second, third, and fourth polarization images are obtained by two polarization imaging devices, and the condition of the object (shape of irregularities on the surface) can be detected on the basis of the difference between the sum of the polarization image L0C0 and the polarization image L90C90 and the sum of the polarization image L90C0 and the polarization image L0C90.

When the average of the images Iav is determined, a brightness image according to the related art obtained by brightness imaging in which non-polarized illumination light is used can be obtained. This is because an image in which the influences of polarizations of the illumination light L and the imaging systems C are all canceled can be obtained, as is clear from the following equation:

$$Iad = [Iav(\|) + Iav(\bot)]/2 = [L0C0 + L0C90 + L90C0 + L90C90]/4$$

Next, the structure of a polarization image processing apparatus according to the present embodiment will be described.

Figure 7:
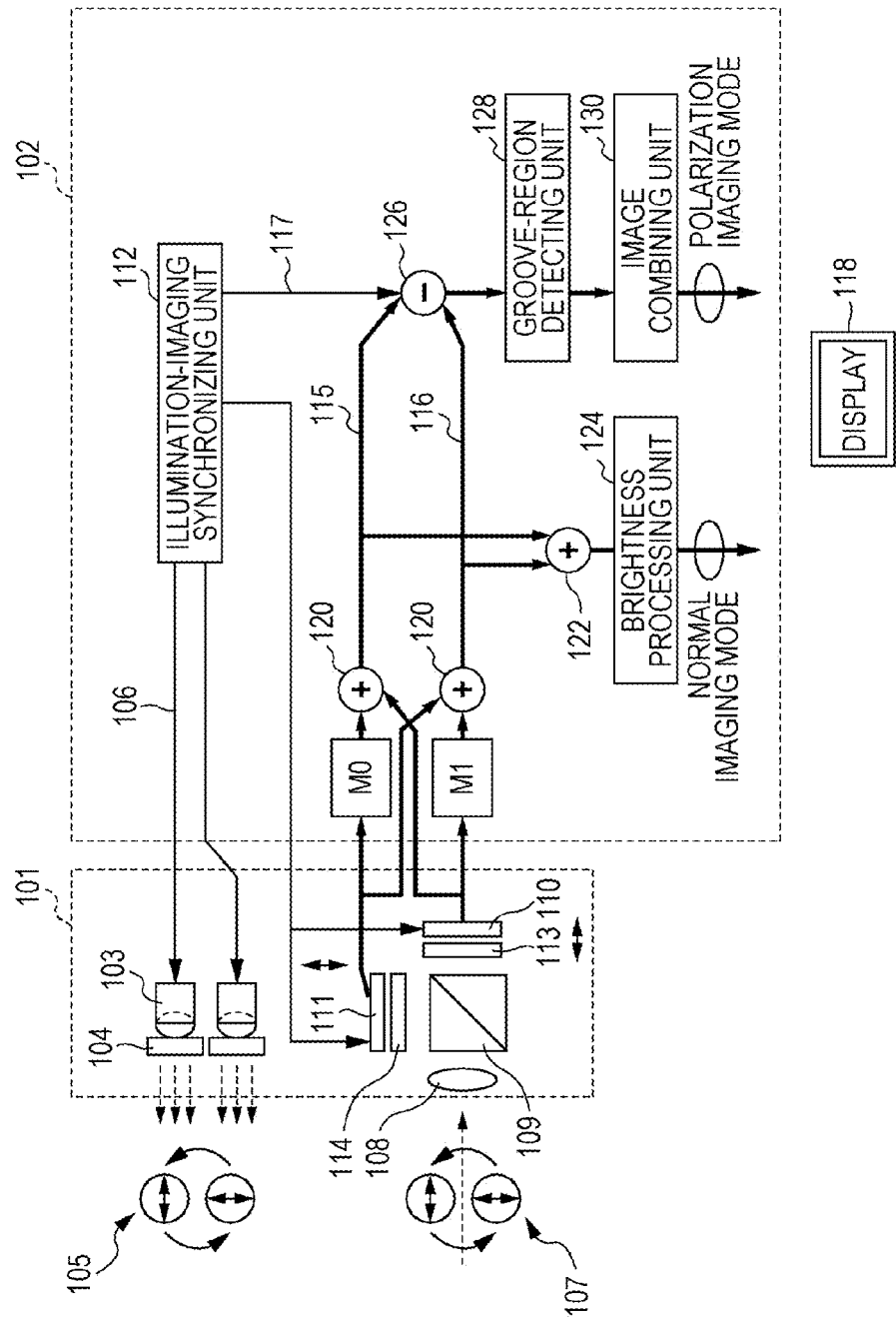
FIG. 7 illustrates a polarization imaging apparatus according to a first embodiment of the present disclosure.

FIG. 7 is a schematic diagram illustrating the overall structure of a polarization image processing apparatus according to the present embodiment. The image processing apparatus may serve as, for example, an endoscope system for inspection. The image processing apparatus according to the present invention serves as a flexible endoscope system, and includes a flexible endoscope 101 that can be inserted into a living body, a control device 102, and a display 118.

In the present embodiment, two types of linearly polarized white light 105, in which the direction of the electric field oscillation plane is 0° and 90°, are temporally alternately emitted toward an object, and returning light 107 that is reflected by the object is divided into two components along two optical paths by a beam splitter 109. The two components into which the returning light 107 has been divided are received by two single-plate color imaging devices 110 and 111 through polarizing plates 113 and 114, respectively, and are subjected to color imaging.

In FIG. 7, polarization imaging is performed at a polarization transmission angle of 0° by the color imaging device 110 and at a polarization transmission angle of 90° by the color imaging device 111. The polarizing plates 113 and 114 may be omitted when the beam splitter 109 is replaced with a polarizing beam splitter.

In the present embodiment, the polarized illumination light 105 is generated by light sources 103 and polarizing plates 104 arranged in an end portion of the endoscope 101. The light sources 103 may be, for example, light emitting diodes (LEDs), lasers, or organic electroluminescent (EL) devices. The timing at which the state of polarization of the illumination light is switched and images are captured is performed is controlled by an illumination-imaging synchronizing unit 112. The captured images are stored in image memories M0 and M1, and an average calculation process, a brightness generation process, and a polarization difference determination process are performed for the stored images and images captured at the next illumination switching time.

The average parallel-Nicols image Iav(∥) and the average crossed-Nicols image Iav(⊥) are temporally alternately transmitted by an image signal 115 and an image signal 116. More specifically, when the polarization direction of the illumination light is 0°, the image signal 115 represents the average parallel-Nicols image Iav(∥) and the image signal 116 represents the average crossed-Nicols image Iav(⊥). In the average polarization difference process, the image signal 116 is subtracted from the image signal 115. When the polarization direction of the illumination light is 90°, the image signal 116 represents the average parallel-Nicols image Iav(∥) and the image signal 115 represents the average crossed-Nicols image Iav(⊥). In the average polarization difference process, the image signal 115 is subtracted from the image signal 116.

The switching control is performed on the basis of a difference direction signal 117. A brightness image generated by a brightness generating unit 122 is displayed on the display 118 as a color moving image of a normal imaging mode by a brightness generating unit 124. The average polarization difference image generated by a polarization difference generating unit 126 is transmitted to a groove-region detecting unit 128. The groove-region detecting unit 128 detects grooves in the small structures on the surface of the object on the basis of the average polarization difference image. An image combining unit 130 generates an image in which the detected grooves are emphasized and displays the generated image on the display 118 as a color image of a polarization imaging mode.

Figure 8A:
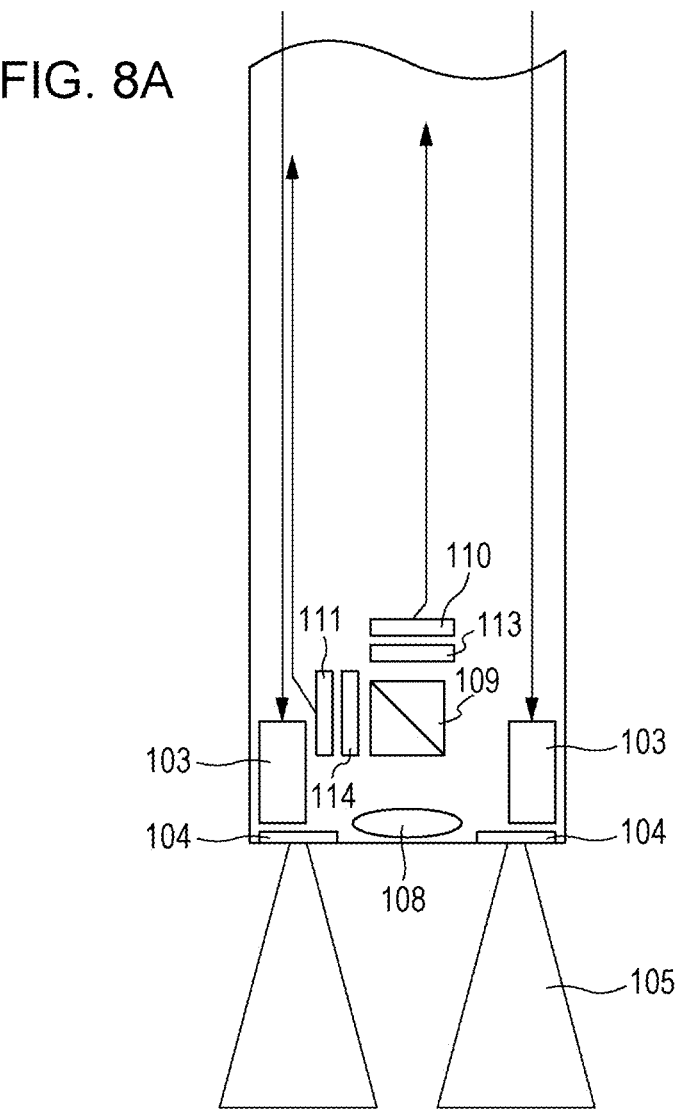
FIGS. 8A and 8B illustrate the structure of an end portion of an endoscope according to the first embodiment of the present disclosure.
Figure 8B:
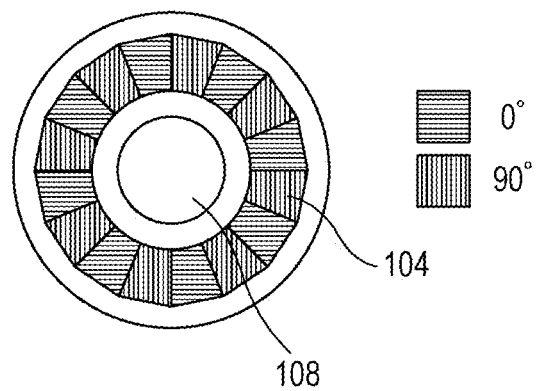

FIG. 8A is a sectional view illustrating an example of the structure of the end portion of the endoscope 101, and FIG. 8B is a front view of the end portion.

As illustrated in FIG. 8B, the light sources 103 and the polarizing plates 104 that cover the respective light sources 103 are arranged in a ring-like pattern at the end of the endoscope. Each light source 103 and the corresponding polarizing plate 104 form a light source segment that can be turned on individually (the number of segments is 16 in FIG. 8B). In this example, the polarization transmission axes of the 16 polarizing plates 104 that are arranged in the ring-like pattern extend in the directions of 0° and 90° alternately. Accordingly, light emitted from the odd-numbered light sources counted from a reference light source is converted into linearly polarized light that is polarized in the direction of 0° by the corresponding polarizing plates 104. Similarly, light emitted from the even-numbered light sources counted from the reference light source is converted into linearly polarized light that is polarized in the direction of 90° by the corresponding polarizing plates 104. The number of light sources 103 (number of segments) is not limited to 16. In addition, the polarizing plates 104 having the polarization transmission axes extending in the direction of 0° and the polarizing plates 104 having the polarization transmission axes extending in the direction of 90° are not necessarily arranged alternately.

The returning light that returns from the object passes through an objective lens 108 that is located around the center of the ring-shaped pattern in which the light sources 103 are arranged, and is guided to a beam splitter 109. The returning light is divided by the beam splitter 109 along two optical paths into two light components, which are processed in parallel by two imaging systems.

In the present embodiment, two groups of light source segments, each group including eight light source segments of the same type that are not next to each other, are alternately selected and turned on, so that the two types of linearly polarized illumination light having orthogonal polarization directions are temporally alternately emitted. As described above, the number of segments and the arrangement of the polarizing plates are not limited. However, preferably, the positions of the light sources that emit light are not shifted by a large amount when the polarization direction of the linearly polarized light is changed.

Figure 9A:
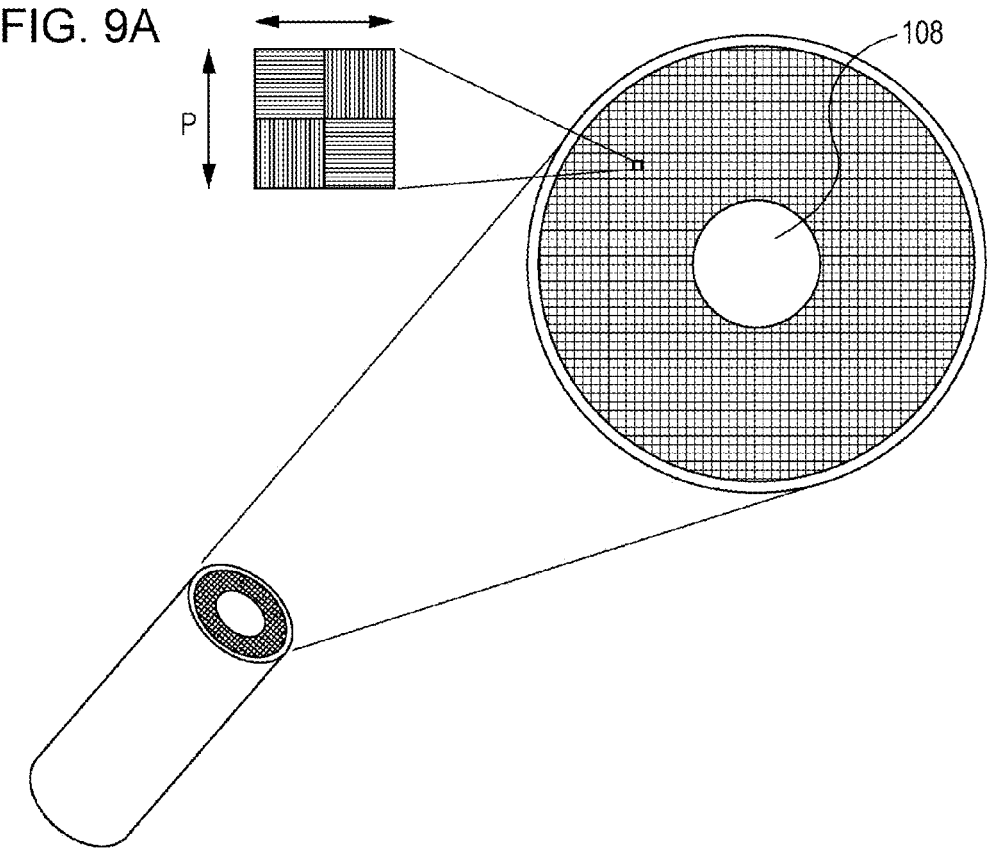
FIGS. 9A and 9B illustrate another example of polarization illumination.

FIG. 9A illustrates another example of an illumination unit that emits polarized illumination light. In this example, the size of illumination pixel units that are successively turned on is sufficiently small, and the number of illumination pixel units is sufficiently large. Thus, the displacement of the positions of light sources that emit light can be reduced to one pixel or less at the imaging side.

Figure 9B:
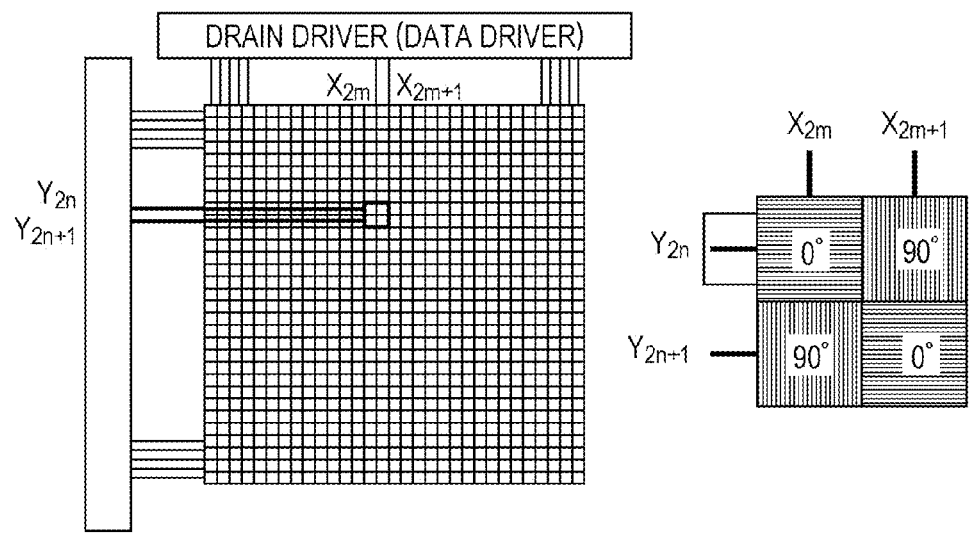

The surface illumination unit illustrated in FIG. 9B includes a plurality of pixels that are arranged two dimensionally. Each pixel is driven by an X-axis data driver and a Y-axis data driver. The pixels that are driven by both the X-axis data driver and the Y-axis data driver emit light.

For example, when signal lines of the X-axis data driver whose X coordinates are $X_{2m}$ and signal lines of the Y-axis data driver whose Y coordinates are $Y_{2m}$ are driven, pixels at coordinates ($X_{2m}$, $Y_{2m}$), where X and Y coordinates are both even numbers, simultaneously emit light. As a result, light having a polarization plane at 0° is emitted.

Similarly, when signal lines of the X-axis data driver whose X coordinates are $X_{2m+1}$ and signal lines of the Y-axis data driver whose Y coordinates are $Y_{2m+1}$ are driven, pixels at coordinates ($X_{2+1m}$, $Y_{2m+1}$), where X and Y coordinates are both odd numbers, simultaneously emit light. Also in this case, light having a polarization plane at 0° is emitted.

However, at pixels where the X coordinate of the signal line driven by the X-axis data driver and the Y coordinate of the signal line driven by the Y-axis data driver are an odd number and an even number, respectively, or an even number and an odd number, respectively, linearly polarized illumination light having a transmission polarization plane at 90° is emitted.

Such a surface illumination unit is advantageous in that the state of polarization of the illumination light can be changed without changing the illuminance and light distribution over the entire area. When the surface light source is used for illumination, the illumination light can be made uniform. As a result, extremely high regular reflection brightness on a surface mucous membrane of an organ can be reduced and the imaging process can be appropriately performed. The illumination unit in which the polarization plane is rotated is not limited to those including light source segments as described above, and a polarization phase shifter, such as a variable retarder, which utilizes the property of liquid crystal may instead be used.

Figure 10:
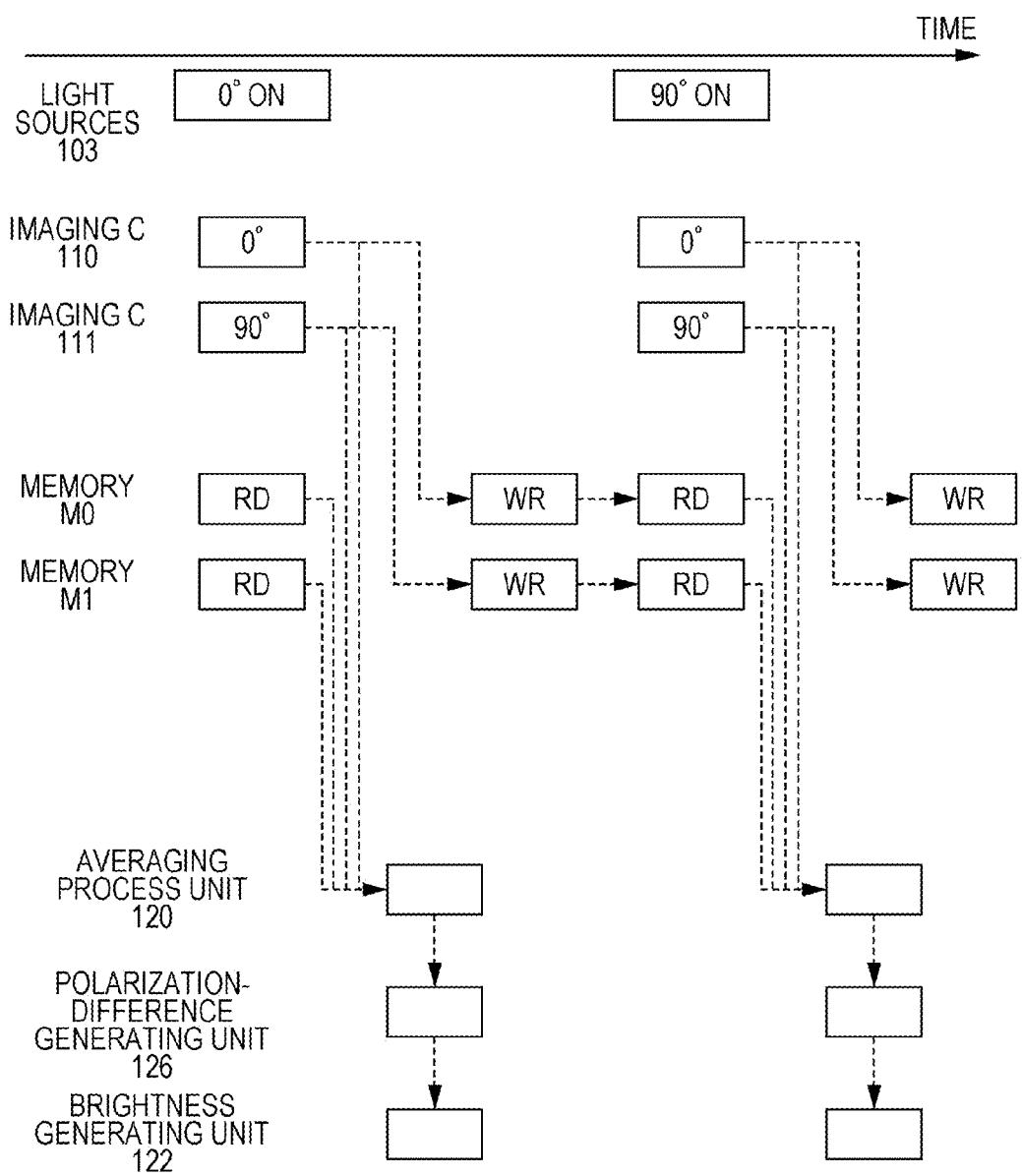
FIG. 10 is a timing chart illustrating the timing for capturing images and reading/writing the images from/to image memories in a polarization imaging mode.

FIG. 10 is a chart showing the timing of illumination and imaging in the polarization imaging mode according to the embodiment illustrated in FIG. 7. FIG. 10 also shows the timing for reading (RD) and writing (WR) image data from/to memories M0 and M1 capable of storing the image data.

The light sources 103 are turned on such that the angle of transmission axis of the linearly polarized light switches between 0° and 90°. During the time in which each type of light is emitted, the imaging device 110 and the imaging device 111 perform polarization imaging to capture images of a single frame with polarization transmission planes of 0° and 90° in parallel. The image data of the captured images is transmitted to an average calculation process unit 120. At the same time, image data of a previous frame that is read from the image memories M0 and M1 is also transmitted to the calculation process unit 120, and is subjected to an average calculation process together with the image data of the captured images.

The average parallel-Nicols image Iav(∥) and the average crossed-Nicols image Iav(⊥) are transmitted to calculation process units, such as the polarization difference generating unit 126 and the brightness generating unit 122. The generated average polarization difference image is transmitted to the groove-region detecting unit 128 and the image combining unit 130, and is displayed on the display 118 as an image of the polarization imaging mode in which small structures on the organ surface are made clear. Also, the generated brightness image is displayed on the display 118 as an image of the normal imaging mode.

Figure 11:
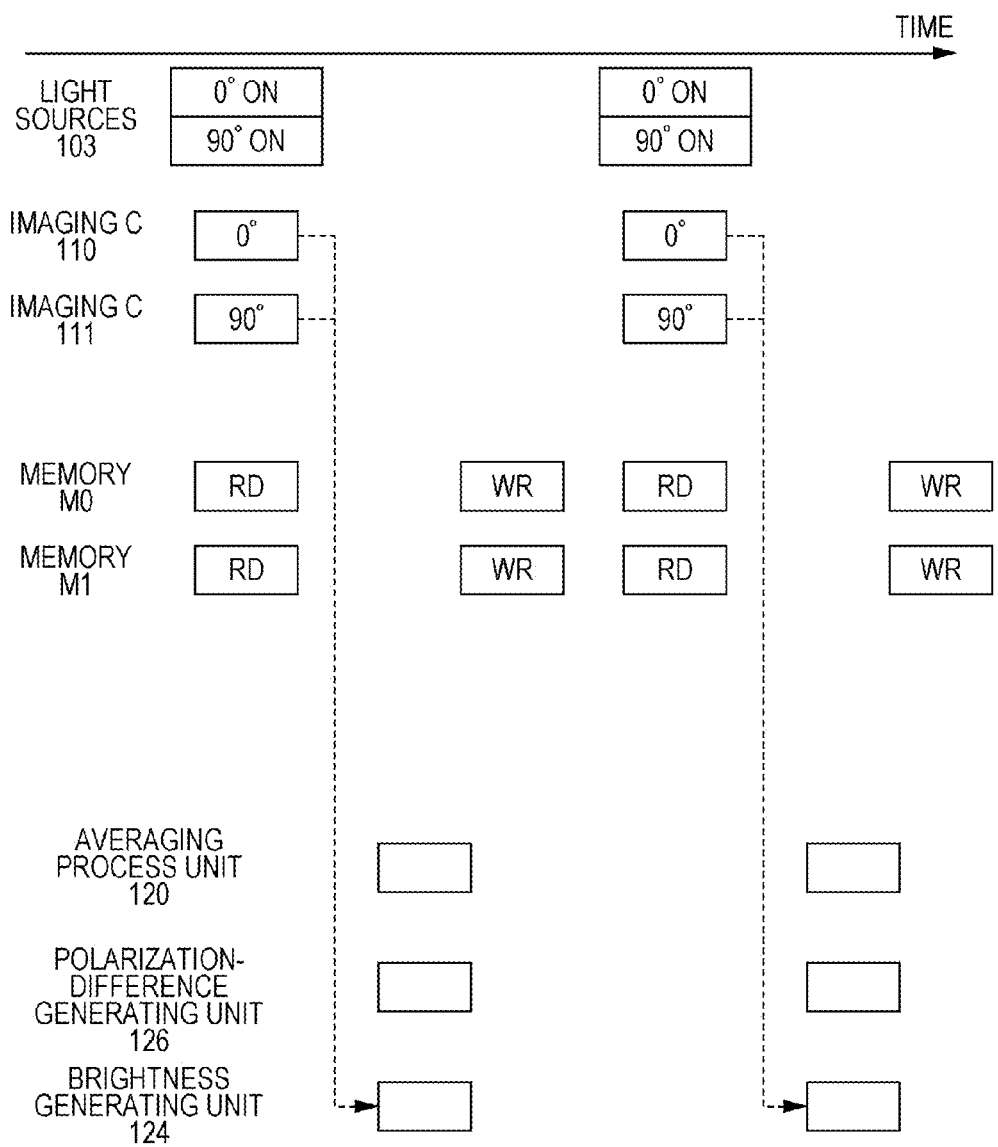
FIG. 11 is a timing chart illustrating the timing for capturing images and reading/writing the images from/to image memories in a normal imaging mode.

FIG. 11 is a chart showing the timing of illumination and imaging in the normal imaging mode according to the embodiment illustrated in FIG. 7. FIG. 11 also shows the timing for reading (RD) and writing (WR) image data from/to the image memories M0 and M1 capable of storing the image data.

The light sources 103 in which the transmission angles of the linearly polarized light are 0° and 90° are simultaneously turned on, so that the emitted light is equivalent to non-polarized light. During the time in which this light is emitted, the imaging device 110 and the imaging device 111 obtain data of images (polarization images) of a single frame with the polarization transmission planes of 0° and 90° in parallel. The obtained image data is transmitted to the brightness generating unit 124, and the average thereof is determined. As a result, polarization imaging is canceled and a normal brightness image is obtained. In this mode, it is not necessary to use the image memories M0 and M1 or the average calculation process unit 120. In addition, since light components having different polarization directions can be emitted at the same time, the amount of illumination light is increased, and the exposure time of the imaging devices is reduced. As a result, a moving image can be captured at a high speed.

Figure 12:
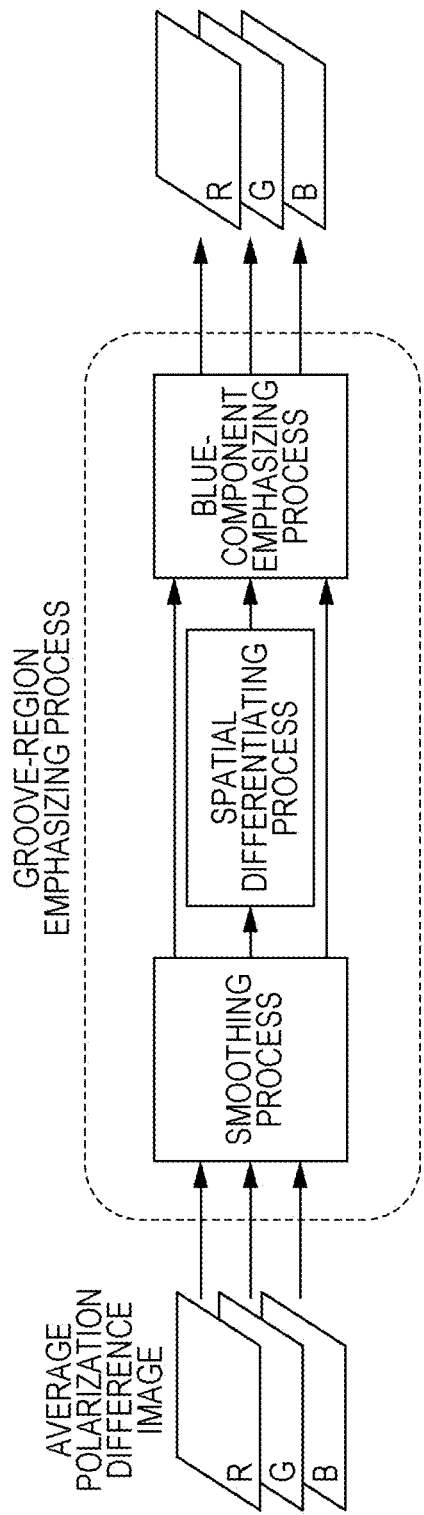
FIG. 12 illustrates a polarization-image emphasizing process performed by a groove-region detecting unit and an image combining unit.

FIG. 12 is a diagram illustrating a polarization-image emphasizing process performed by the groove-region detecting unit 128 and the image combining unit 130.

The polarization-image emphasizing process will now be described with reference to FIGS. 12 and 13 on the assumption that an average polarization difference image has been acquired. A groove-region emphasizing process includes a smoothing process, a spatial differentiating process, and a blue-component emphasizing process.

(1) Smoothing Process

Figures 13A, 13B:
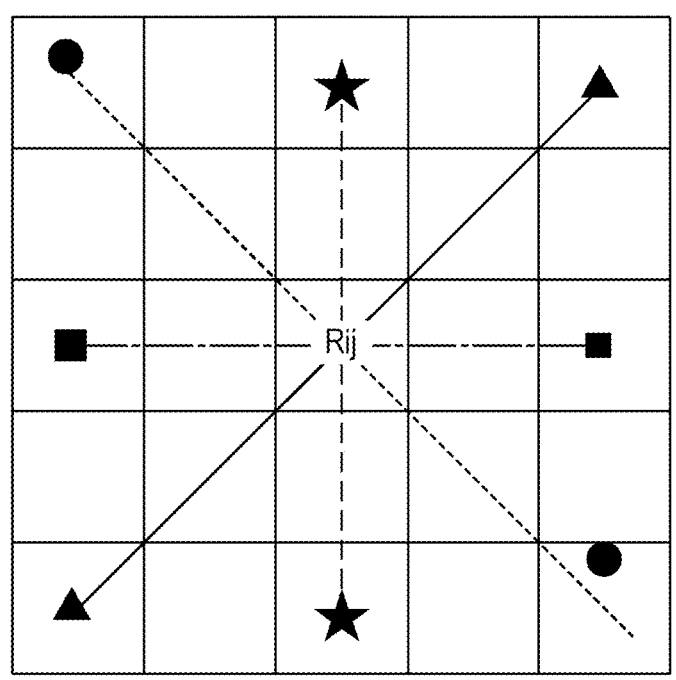
FIGS. 13A and 13B illustrate examples of a smoothing filter and a differentiating filter, respectively.

Before the input image is subjected to the differentiating process, a high-frequency noise component having a frequency higher than that of the texture to be emphasized is removed from the image. More specifically, to remove the noise component, a smoothing filter process is performed. In the present embodiment, a common Gaussian filter is used. By making the mask size of the filter the same as the mask size of a differential mask filter, which will be described below, small granular noise can be prevented from being emphasized. FIG. 13A shows an example of a smoothing filter having a size of 5×5. An image of 1024×768 pixels may be reduced to an image of 512×384 pixels by using this smoothing filter.

(2) Differentiating Process

A G-component image that has been subjected to the smoothing process is subjected to a differentiating process as described below to detect pixel regions that are darker than the surrounding regions. The reason why the image regions that are darker than the surrounding regions are detected is because, as described above with reference to FIG. 1, when the polarization direction of the polarized illumination light is at an angle of about 0° to 45° with respect to the grooves in the surface of the object, the brightness contrast is high and the grooves appear darker than the surrounding regions. In the differentiating process, a differentiating filter that specifies the central and peripheral pixels as illustrated in FIG. 13B (5×5 pixels in this example) is set for the image that has been subjected to the smoothing process. Although various types of differential filters may be used, in this example, a differential filter suitable for emphasizing mesh-shaped grooves in the surface with high continuity is used. In the region of 5×5 pixels, the following process is performed.

(i) A pixel value Rij at the central pixel is compared with pixel values of pixels on both sides of the central pixel in a horizontal direction (black squares), a vertical direction (black starts), an oblique direction toward the upper right (black triangles), and an oblique direction toward the lower right (black circles), and the differences therebetween are determined.

(ii) When the pixel value at the central pixel is higher than both of the pixel values at the pixels on both sides of the central pixel in one of the four directions, it is determined that the central pixel is recessed.

(iii) The absolute value of the maximum difference in the four directions is determined as $\Delta$, and $\Delta C$, which is the product of $\Delta$ and a predetermined constant, is determined as the result of the spatial differentiating process.

(3) Emphasizing of Blue Component

A blue component is emphasized by subtracting the value of $\Delta C$ from R and G components. If the R and G components become less than or equal to 0, the shortfall is to be covered by other color components to maintain the continuity. Therefore, although the color phase varies depending on the magnitude of $\Delta$, smooth connection can be realized. The lower one of the values of the R and G components is defined as C1, and the higher one of the values of the R and G components is defined as C2. Then, one of the three types of processes described below is performed in accordance with C1 and C2.

FIG. 14 illustrates the three types of processes performed in respective cases.

1) When $\Delta C$ is lower than or equal to C1, a process of subtracting $\Delta C$ from the R and G signals is performed. 2) When $\Delta C$ exceeds C1, the signal with the minimum value is reduced to zero, and the remainder is subtracted from the signal with the intermediate value. 3) When the R and G signals are both reduced to zero, the remainder is subtracted from the B signal.

With the above-described process, in a color signal of a pixel region in which the central pixel is brighter than the surrounding pixels, blue color is emphasized in accordance with how bright the central pixel is. As a result, a color image similar to that obtained when indigo carmine is sprayed can be obtained.

When $\Delta C \leq C1$    1)

C1=C1−$\Delta C$, C2=C2−$\Delta C$

When $C1 < \Delta C \leq (C1+C2)/2$    2)

C1=0, C2=(C1+C2)−(2$\Delta C$)

When $(C1+C2)/2 < (\Delta C)$    3)

C1=0, C2=0, B=B−((2$\Delta C$)−C1−C2)

Figure 15A:
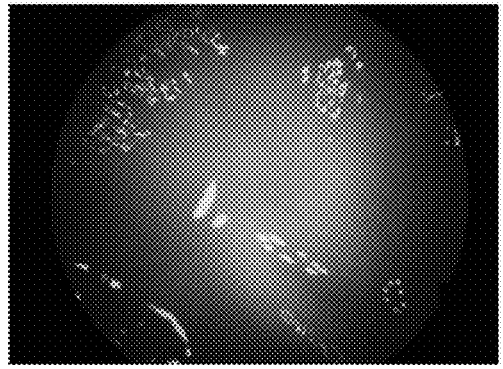
FIGS. 15A to 15D illustrate the results of image processing of a pig stomach.
Figure 15B:
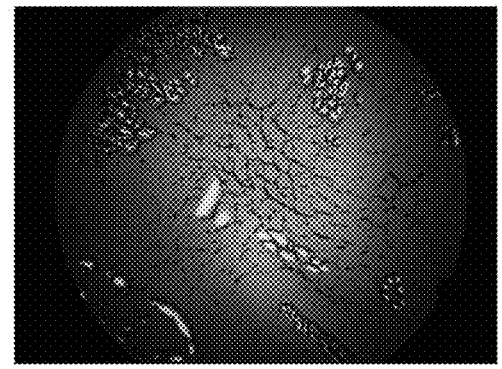
Figure 15C:
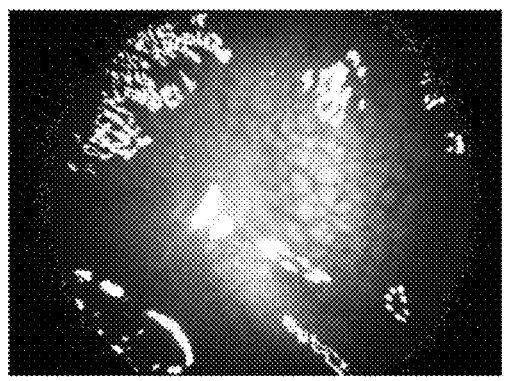
Figure 15D:
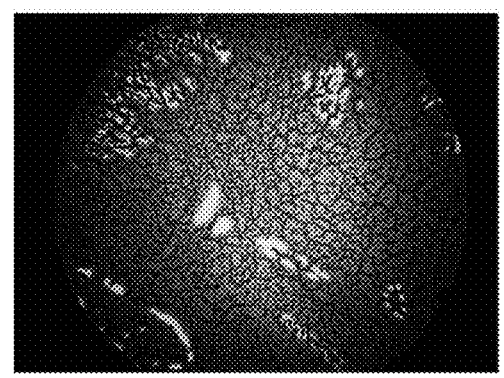

FIGS. 15A to 15D illustrate the results of image processing performed by an experimental model of a polarization imaging apparatus according to the first embodiment of the present disclosure when the object is a pig gastric mucous membrane. FIG. 15A is a color brightness image of the pig stomach. Although large recesses and projections on the surface and halation can be observed, small structures on the surface cannot be observed. FIG. 15B illustrates the result of a groove-region emphasizing process according to the related art performed by brightness image processing. More specifically, the process of FIG. 12 is performed on the color brightness image. Although large recesses and projections are detected and emphasized, the result is not sufficiently satisfactory. FIG. 15C illustrates an average polarization difference image obtained by using an average parallel-Nicols image and an average crossed-Nicols image. The groove regions on the surface are dark and the contrast is increased. FIG. 15D is the result obtained by subjecting the average polarization difference image illustrated in FIG. 15C to the groove-region emphasizing process. Compared to FIG. 15B, according to the present method, the small structures on the surface are reliably detected in more detail.

First Modification of First Embodiment

Figure 16A:
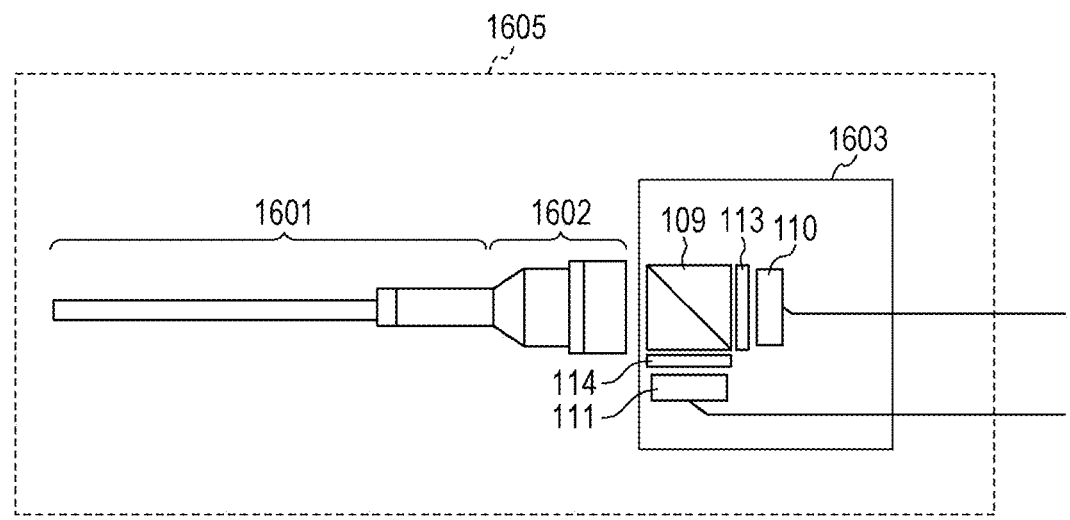
FIGS. 16A and 16B illustrate the structure of a rigid endoscope according to a first modification of the first embodiment of the present disclosure.
Figure 16B:
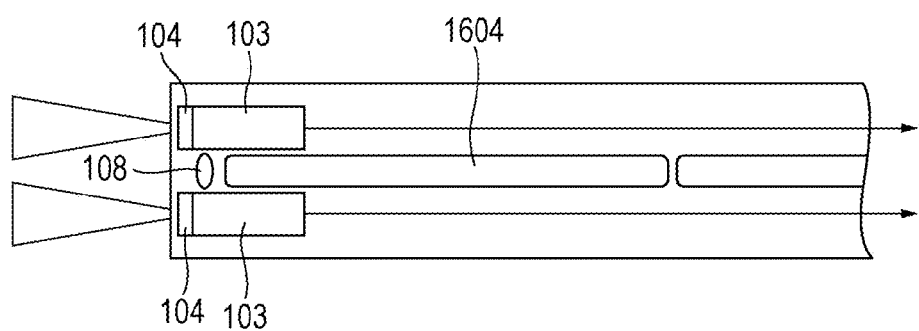

FIGS. 16A and 16B illustrate a first modification of the first embodiment of the present disclosure. This modification differs from the above-described structure in that the flexible endoscope 101 illustrated in FIG. 7 is replaced by a rigid endoscope. As illustrated in FIG. 16A, a rigid endoscope 1605 according to this modification includes three portions, which are an end portion 1601 formed of a pipe having relay lenses disposed therein, a connecting optical system 1602, and a proximal polarization camera 1603. The proximal polarization camera 1603 divides an optical path with a beam splitter similar to that in the first embodiment to acquire a color image and a polarization image of an object at the same time. FIG. 16B illustrates the inner structure of the end portion 1601. The end portion 1601 includes an illumination unit including light sources 103 and polarizing plates 104, an objective lens 108 that receives returning light, and a plurality of relay lenses 1604 for optically guiding an image to the proximal polarization camera 1603. The returning light, which returns from the object, is guided through the end portion 1601 by the relay lenses 1604 while the state of polarization thereof is maintained. An image circle is magnified and corrected by the connecting optical system 1602, and is captured by the proximal polarization camera 1603. Components having the same structures as those illustrated in FIG. 10 are denoted by the same reference numerals, and descriptions thereof are thus omitted. Also in this modification, the operations in the normal imaging mode and the polarization imaging mode are performed at the timing shown in the timing charts of FIGS. 10 and 11.

In the endoscope system including the rigid endoscope 1605, a function of controlling the halation of the illumination light is important since it is essential to make the field of view clear during a surgery, in addition a flexible endoscope for inspection. In general, to reduce halation in the case where non-polarized light is used, a special light source arrangement that satisfies the Brewster angle is necessary. However, in an endoscope in which polarized illumination light is used, when a crossed-Nicols image is captured for the polarized illumination light, halation can be reduced even in the case of coaxial illumination. However, to reduce strong regular reflection of the light sources, the optical extinction ratio for the polarized light needs to be high. According to the experiment conducted by the present inventor, an optical extinction ratio needs to be 100:1 to 3000:1 or more. If this condition is not satisfied, for example, when the optical extinction ratio is about 80:1, halation cannot be sufficiently reduced and images of the light sources cannot be removed from an image of a smooth object surface.

Figure 17:
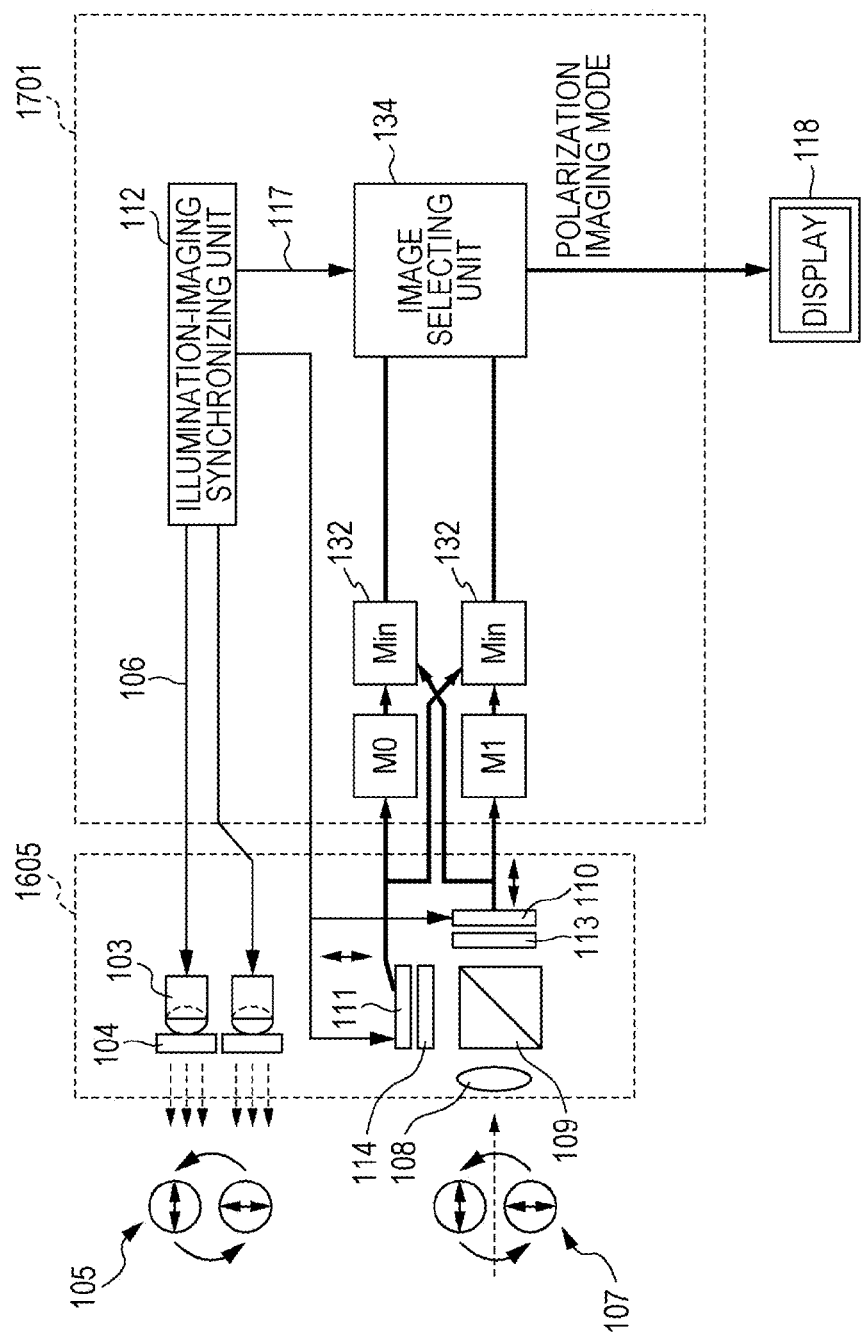
FIG. 17 illustrates the structure of a polarization imaging apparatus according to the first modification of the first embodiment of the present disclosure.

FIG. 17 illustrates an example of the structure for controlling halation. The apparatus illustrated in FIG. 17 includes the rigid endoscope 1605 and a control device 1701. Two types of crossed-Nicols images L0C90 and L90C0 are alternately captured by imaging devices 110 and 111. Therefore, by using the smaller value of the two for each pixel, a crossed-Nicols image with a lower brightness (darker crossed-Nicols image) can be synthesized. This process is performed by a minimization process unit 132, which selects the lower one of two values, and a pixel selecting unit 134 that selects a crossed-Nicols image.

Figure 18A:
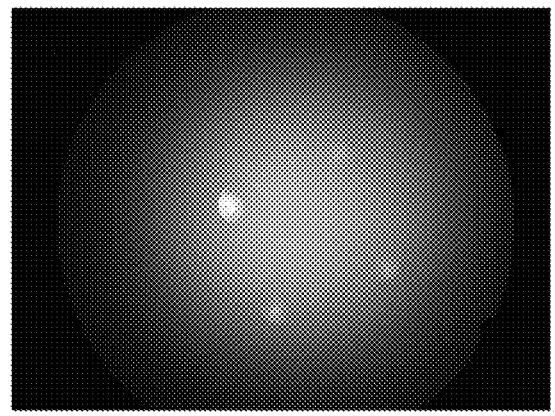
FIGS. 18A, 18B, and 18C illustrate the results of halation control in the case where images of a smooth acrylic plate are captured.
Figure 18B:
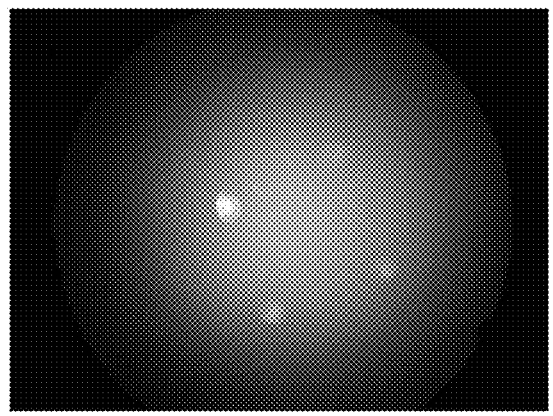
Figure 18C:
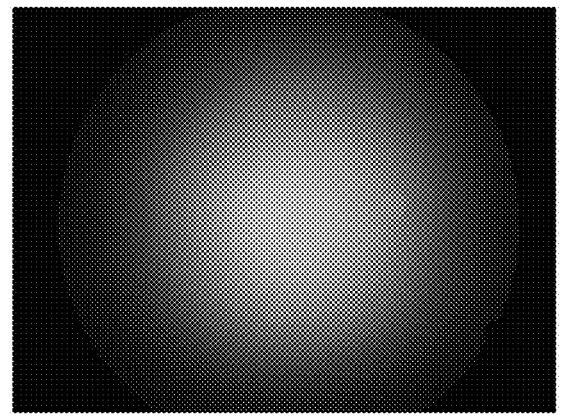

FIGS. 18A to 18C illustrate images obtained by the rigid endoscope illustrated in FIG. 16 when the object is a smooth acrylic plate. FIGS. 18A and 18B illustrate examples of crossed-Nicols images captured to reduce halation of the illumination light at the end of the endoscope. FIGS. 18A and 18B illustrate a crossed-Nicols image L0C90 and a crossed-Nicols image L90C0, respectively. It is clear that since the optical extinction ratio of the polarizing plates included in the rigid endoscope 1605 is about 80:1, halation of the LED light source segments is not sufficiently reduced and still remains. FIG. 18C shows an image obtained by the process illustrated in FIG. 17. As is clear from FIG. 18C, the light source images are substantially completely removed, and reduction in the halation is achieved.

Second Modification of First Embodiment

Figure 19:
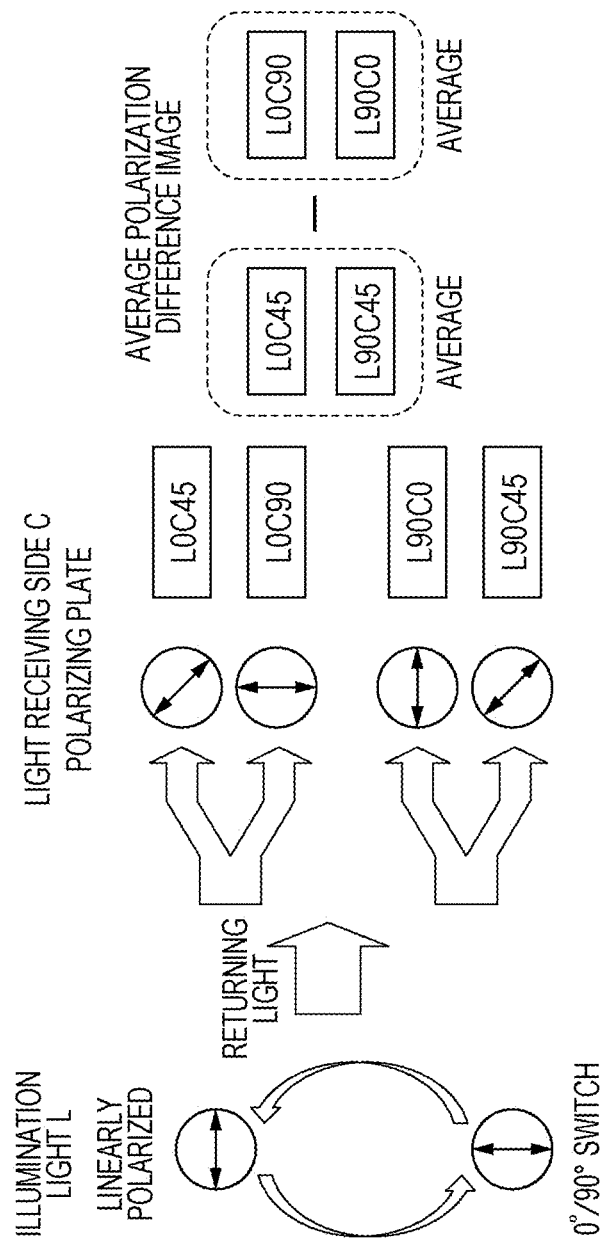
FIG. 19 illustrates a polarization imaging method according to a second modification of the first embodiment of the present disclosure.

FIG. 19 illustrates a second modification of the first embodiment of the present disclosure. In the embodiment described with reference to FIG. 6, the polarizing plates at the light receiving side C have transmission axes in two directions: 0° and 90°. This modification differs from the embodiment illustrated in FIG. 6 in that polarizing plates at the light receiving side C have transmission axes in three directions: 0°, 45°, and 90°. In other words, in the embodiment illustrated in FIG. 6, images L0C0 and L90C90 obtained while the polarizing directions (transmission axis directions) of the polarizing plates of the imaging systems are parallel to the polarizing direction of the illumination light are used as the parallel-Nicols images. In contrast, in the second modification, images L0C45 and L90C45 obtained while the polarizing directions of the polarizing plates are at an angle of 45° with respect to the polarizing direction of the illumination light are used. These images may be referred to as "oblique-Nicols image". Accordingly, in the polarization imaging mode, when halation of the parallel-Nicols images in the polarization difference images is too large due to inclination or smoothness of the surface of the object, the halation can be reduced.

Figure 20:
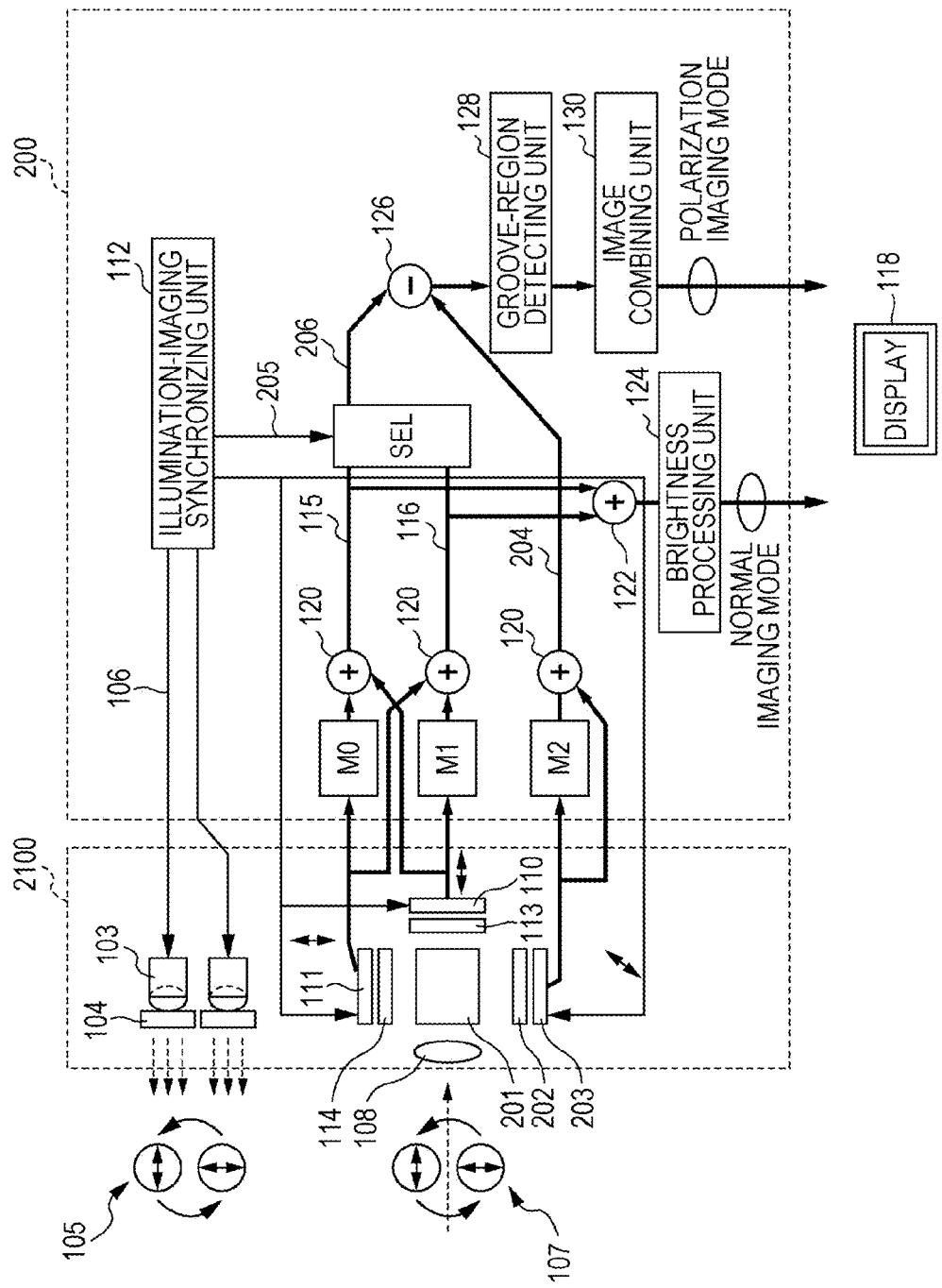
FIG. 20 illustrates the structure of a polarization imaging apparatus according to the second modification of the first embodiment of the present disclosure.

FIG. 20 is a schematic diagram illustrating the overall structure of an image processing apparatus according to the second modification. The image processing apparatus may serve as, for example, an endoscope system for surgery. The image processing apparatus according to the present modification serves as a rigid endoscope system, and includes a rigid endoscope 2100 that can be inserted into a living body, a control device 200, and a display 118.

In the present modification, two types of linearly polarized white light 105, in which the direction of the electric field oscillation plane is 0° and 90°, are temporally alternately emitted. Returning light 107 that is reflected by an object is divided into three light components along three optical paths by a beam splitter 201. The three light components are caused to pass through polarizing plates 113, 114, and 202, and are subjected to color imaging by three single-plate color imaging devices 110, 111, and 203. In the example illustrated in FIG. 20, polarization imaging is performed at a polarization transmission angle of 0° by the color imaging device 110, at a polarization transmission angle of 90° by the color imaging device 111, and at a polarization transmission angle of 45° by the color imaging device 203.

The timing at which the state of polarization of the illumination light is switched and images are captured is controlled by an illumination-imaging synchronizing unit 112. The captured images are stored in image memories M0, M1, and M2. These images and images captured at the next illumination switching time are subjected to an average calculation process, a brightness generation process, and a polarization difference determination process.

The average parallel-Nicols image Iav(∥) and the average crossed-Nicols image Iav(⊥) are temporally alternately represented by an image signal 115 and an image signal 116. More specifically, when the polarization direction of the illumination light is 0°, the image signal 116 represents the average crossed-Nicols image Iav(⊥). When the polarization direction of the illumination light is 90°, the image signal 115 represents the average crossed-Nicols image Iav(⊥). The selection between them is performed by a selecting unit SEL in accordance with a signal 205. An image corresponding to the average parallel-Nicols image (average oblique-Nicols image) is an average image of the image L0C45 and the image L90C45, and is therefore represented by an image signal 204 obtained as a result of an average calculation process performed by using the image read from the memory M2 and the image captured by the color imaging device 203.

An average polarization difference generating unit 126 subtracts an output 206 of the selecting unit SEL from the image signal 204. A brightness image generated by a polarization-difference brightness generating unit 122 is displayed on the display 118 as a color moving image of a normal imaging mode by a brightness generating unit 124. The average polarization difference image generated by the average polarization difference generating unit 126 is transmitted to a groove-region detecting unit 128. The groove-region detecting unit 128 detects grooves in the small structures on the surface of the object on the basis of the polarization difference image. An image combining unit 130 generates an image in which the detected grooves are emphasized and displays the generated image on the display 118 as a color image of a polarization imaging mode.

Figure 21:
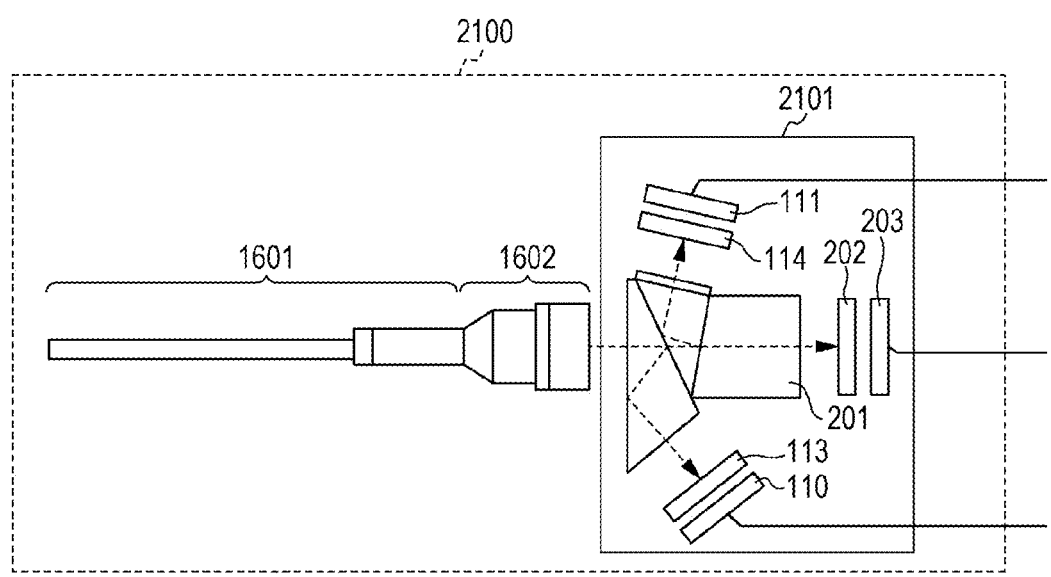
FIG. 21 illustrates the structure of a rigid endoscope according to the second modification of the first embodiment of the present disclosure.

FIG. 21 illustrates the rigid endoscope 2100. The rigid endoscope 2100 illustrated in FIG. 21 includes a proximal polarization camera 2101 having a structure different from that of the rigid endoscope illustrated in FIG. 16. More specifically, to obtain the color image and three types of polarization images of the object at the same time, the beam splitter 201 divides white light along three optical paths. The beam splitter 201 divides the white light into three light components without changing the state of polarization thereof. The three light components are caused to pass through the polarizing plate 113 having a transmission polarization angle of 0°, the polarizing plate 114 having a transmission polarization angle of 90°, and the polarizing plate 202 having a transmission polarization angle of 45°, and images thereof are captured in parallel by the three single-plate color imaging devices 110, 111, and 203.

In this example, the single-plate color imaging device 203 having a polarization transmission axis in the direction of 45° is used as the third polarization imaging device. However, the direction of the polarization transmission axis may be another angle in the range in which halation can be suppressed.

Second Embodiment

Figure 22:
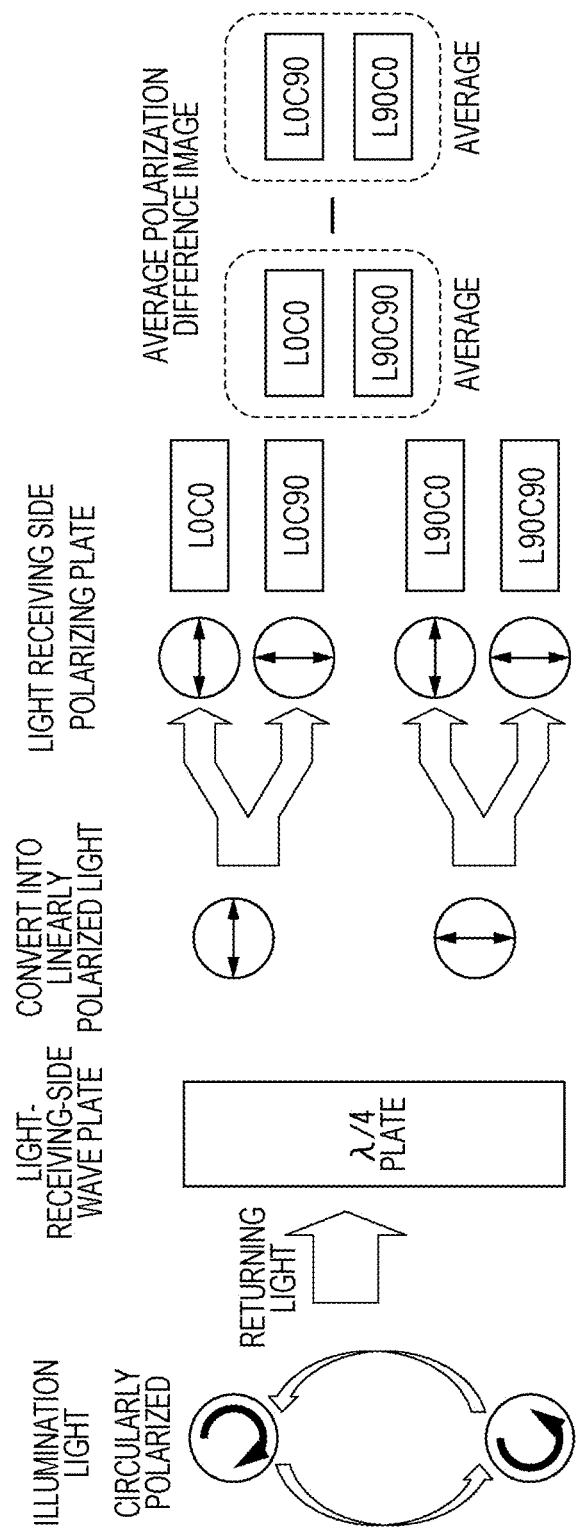
FIG. 22 illustrates a polarization imaging method according to a second embodiment of the present disclosure.

FIG. 22 illustrates a polarization imaging method according to a second embodiment of the present disclosure. In the present embodiment, circularly polarized light is used as illumination light instead of linearly polarized light. By using circularly polarized light, grooves having a random direction distribution in the surface of the object can be evenly detected.

In the present embodiment, an object is illuminated with illumination light L, which is circularly polarized light having an electric field oscillation plane that temporally alternately rotates clockwise and counterclockwise on a plane perpendicular to the travelling direction of the light.

Although the direction of circular polarization is normally defined as a direction when viewed in the light travelling direction, in this embodiment, the direction of circular polarization is always defined as a direction when viewed from the camera. In this coordinate system, the direction of circular polarization of the circularly polarized light that is perpendicularly incident on a smooth flat surface does not change even when the light is reflected.

A receiving camera C receives returning light, changes the phase of the light with a $\lambda/4$ plate to convert the light into linearly polarized light, and then divides the linearly polarized light into two light components. Then, two types of polarization imaging processes are performed in parallel by using linear polarizing filters having polarization transmission axes in the directions of 0° (horizontal) and 90° (vertical) along a plane, similar to the illumination light. The $\lambda/4$ plate is an example of a phase shift element that is arranged so as to allow the returning light that returns from the object to pass therethrough, the phase shift element converting clockwise polarized light into light polarized in a first direction and counterclockwise polarized light into light polarized in a second direction that is orthogonal to the first direction. For clockwise circularly polarized illumination light L, a parallel-Nicols image L0C0 and a crossed-Nicols image L0C90 are obtained. For counterclockwise circularly polarized illumination light L, a crossed-Nicols image L90C0 and a parallel-Nicols image L90C90 are obtained.

FIGS. 23 and 24 illustrate the manner in which the returning circularly polarized light that is reflected by the object is converted into two types of linearly polarized light having orthogonal polarization directions. FIG. 23 illustrates the manner in which counterclockwise circularly polarized light 2301 passes through the $\lambda/4$ plate are returning light, and is thereby converted into linearly polarized light 2303. In the counterclockwise circularly polarized light 2301, the phase of a Y-axis electric field component Ey is delayed by $\lambda/4$ with respect to the phase of an X-axis electric field component Ex.

Accordingly, as in an orientation 2302 of the $\lambda/4$ plate, the X-axis and Y-axis are respectively set to an F-axis (fast or advanced axis) and an S-axis (slow or delayed axis), so that the phase of Ex is further advanced by $\lambda/4$ as shown by the arrow in 2304 and the phase difference between Ex and Ey is changed to $\lambda/2$, that is, $\pi$. As a result, linearly polarized light having an angle of $\theta=135°$ can be obtained as in 2303.

FIG. 24 illustrates the manner in which the clockwise circularly polarized light 2401 passes through the $\lambda/4$ plate as returning light, and is thereby converted into linearly polarized light 2403. In the clockwise circularly polarized light 2401, the phase of the Y-axis electric field component Ey is advanced by $\lambda/4$ with respect to the phase of the X-axis electric field component Ex. Accordingly, as in the orientation 2302 of the $\lambda/4$ plate, the X-axis and Y-axis are respectively set to the F-axis (fast or advanced axis) and the S-axis (slow or delayed axis), so that the phase of Ex is further advanced by $\lambda/4$ as shown by the arrow in 2404 and the phase difference between Ex and Ey is changed to 0. As a result, linearly polarized light having an angle of $\theta=45°$ can be obtained as in 2403.

Figure 25:
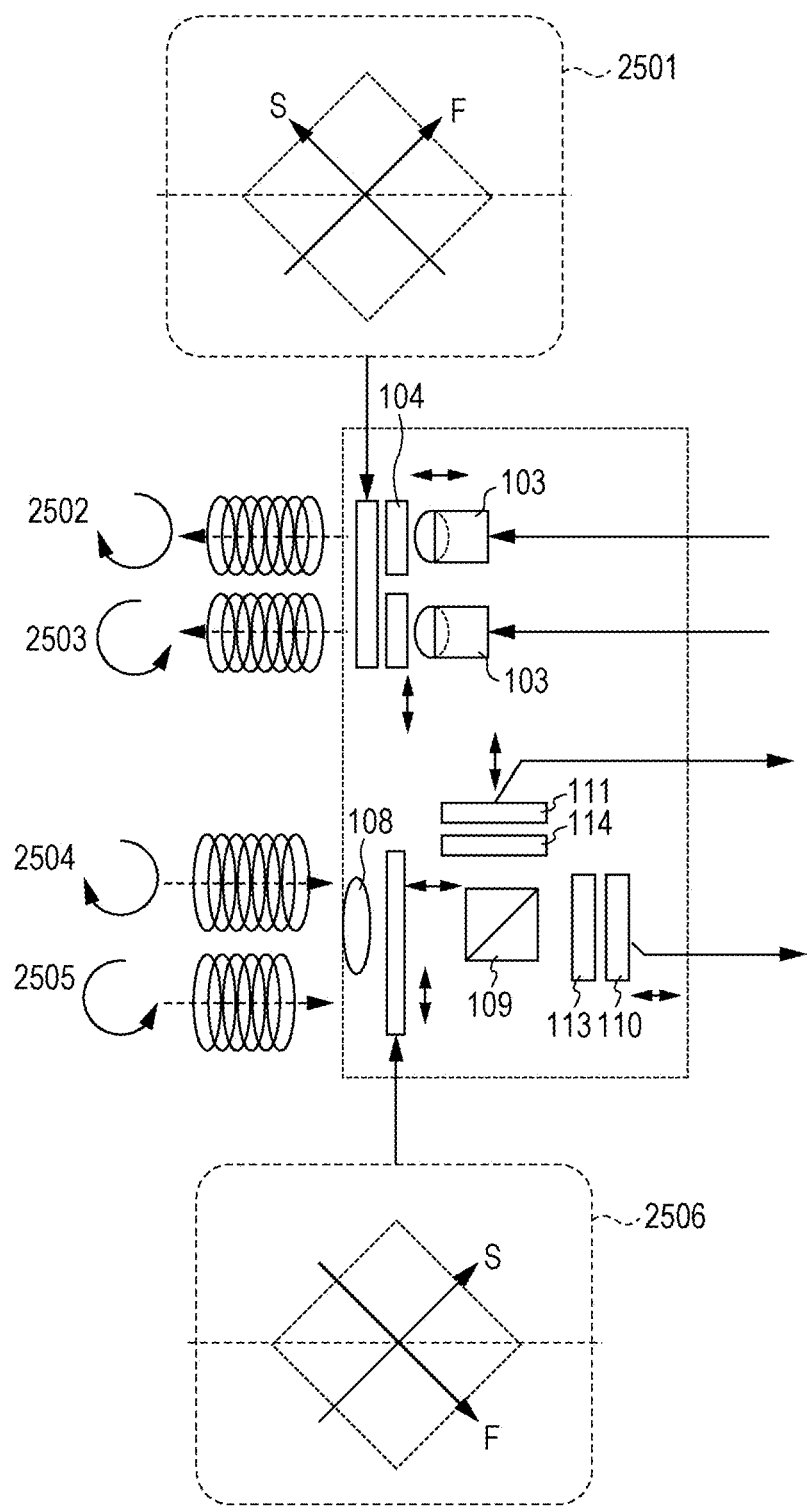
FIG. 25 illustrates the structure of an end portion of a polarization imaging apparatus according to the second embodiment of the present disclosure.

FIG. 25 is a schematic diagram illustrating the structure of a part of an image processing apparatus according to a second embodiment of the present disclosure. The image processing apparatus serves as a flexible endoscope for inspection or a rigid endoscope for surgery. The overall structure of this apparatus is the same as that of the apparatus illustrated in FIG. 7. Therefore, only an end portion of an endoscope 101, which differs from that in the apparatus illustrated in FIG. 7, will be described.

The illumination unit included in the end portion of the endoscope of the apparatus illustrated in FIG. 25 includes a $\lambda/4$ plate 2501, polarizing plates 104, and light sources 103 arranged in that order from the object side. The light sources 103 are structured such that light source elements that emit linearly polarized light having a polarization plane at 0° and light source elements that emit linearly polarized light having a polarization plane at 90° are alternately arranged in a circular pattern. The number of light source elements is, for example, eight. The $\lambda/4$ plate 2501 is arranged such that optical axes, which are an F-axis (fast or advanced axis) and an S-axis (slow or delayed axis), thereof are at an angle of 45° with respect to the polarization plane of the light that is emitted from the light sources 103 and transmitted through the polarizing plates 104, so that the phase can be shifted by $\lambda/4$. Here, the array of light source elements having a polarization plane at 0° and the array of light source elements having a polarization plane at 90° are alternately selected and turned on. Accordingly, the object can be substantially spatially evenly illuminated with illumination light that temporally alternately switches between clockwise circularly polarized illumination light 2502 and counter-clockwise circularly polarized illumination light 2503.

The two types of circularly polarized light are emitted toward and reflected by the object, and return to the camera side as partially polarized returning light in which the degree of polarization is reduced. In accordance with the state of circular polarization of the circularly polarized illumination light, clockwise circularly polarized light 2504 and counterclockwise circularly polarized light 2505 alternately return. The returning light passes through an objective lens 108, and is alternately converted into two types of linearly polarized light having orthogonal polarization directions by a $\lambda/4$ plate 2506. The $\lambda/4$ plate 2506 is arranged such that optical axes, which are an F-axis (fast or advanced axis) and an S-axis (slow or delayed axis), thereof are at an angle of 45° with respect to the polarizing filters at the imaging device side. Each of the two types of linearly polarized light is divided into two light components by a beam splitter 109 along optical paths. The light components pass through polarizing filters 114 and 113, and reach imaging devices 111 and 110, where polarization imaging is performed.

Third Embodiment

Figure 26:
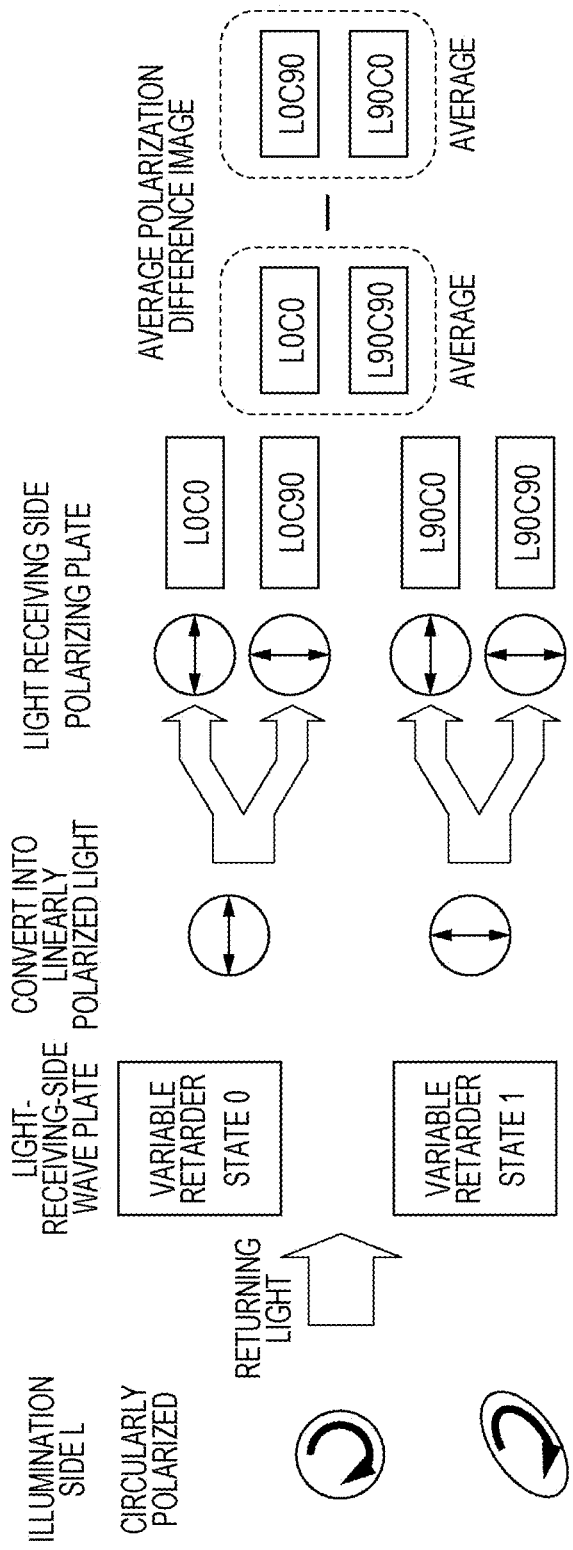
FIG. 26 illustrates a polarization imaging method according to a third embodiment of the present disclosure.

FIG. 26 illustrates an imaging method according to a third embodiment of the present disclosure. Similar to the second embodiment, in the present embodiment, circularly polarized light is used as illumination light. The third embodiment differs from the second embodiment in that only circularly polarized light having a single polarization direction is used as illumination light. Accordingly, the structure of the illumination unit included in an end portion of an endoscope can be simplified, and grooves having a random direction distribution on the surface of the object can be evenly detected.

An object is illuminated with illumination light L, which is circularly polarized light having an oscillation plane that clockwise or counterclockwise on a plane perpendicular to the travelling direction of the light. Although the direction of circular polarization is not limited, here, it is assumed that the direction of circular polarization is clockwise when viewed from the camera.

A receiving camera C receives returning light, and converts the returning light into linearly polarized light by shifting the phase of an oscillating component of the returning light with a variable retarder (variable phase shift element). After that, the linearly polarized light is divided into two light components, and two types of polarization imaging processes are performed in parallel by using linear polarizing filters having polarization transmission axes in the directions of 0° (horizontal) and 90° (vertical) along a plane. The variable retarder is a so-called phase shifter which uses liquid crystal. By utilizing the technology of, for example, Liquid Crystal Variable Retarders (manufactured by Meadowlark Optics Inc.), the phase of the oscillating component can be changed by an amount of 0 to $\lambda/2$ by controlling the applied voltage. Therefore, the circularly polarized light can be converted into two types of linearly polarized light having orthogonal polarization directions. The variable retarder is an example of a variable phase shift element that is arranged so as to allow the returning light that returns from the object to pass therethrough, the variable phase shift element operating in a first mode and a second mode alternately, the returning light being converted into light in a first state of polarization that is polarized in a first direction in the first mode and being converted into light in a second state of polarization that is polarized in a second direction in the second mode, the second direction being orthogonal to the first direction. More specifically, in the case where the circularly polarized illumination light L is clockwise, the voltage applied to the variable retarder can be temporally controlled so that, for example, a parallel-Nicols image L0C0 and a crossed-Nicols image L0C90 are obtained when the state of the variable retarder is 0, and an image L90C0 and a parallel-Nicols image L90C90 are obtained when the state of the variable retarder is 1.

Figure 27:
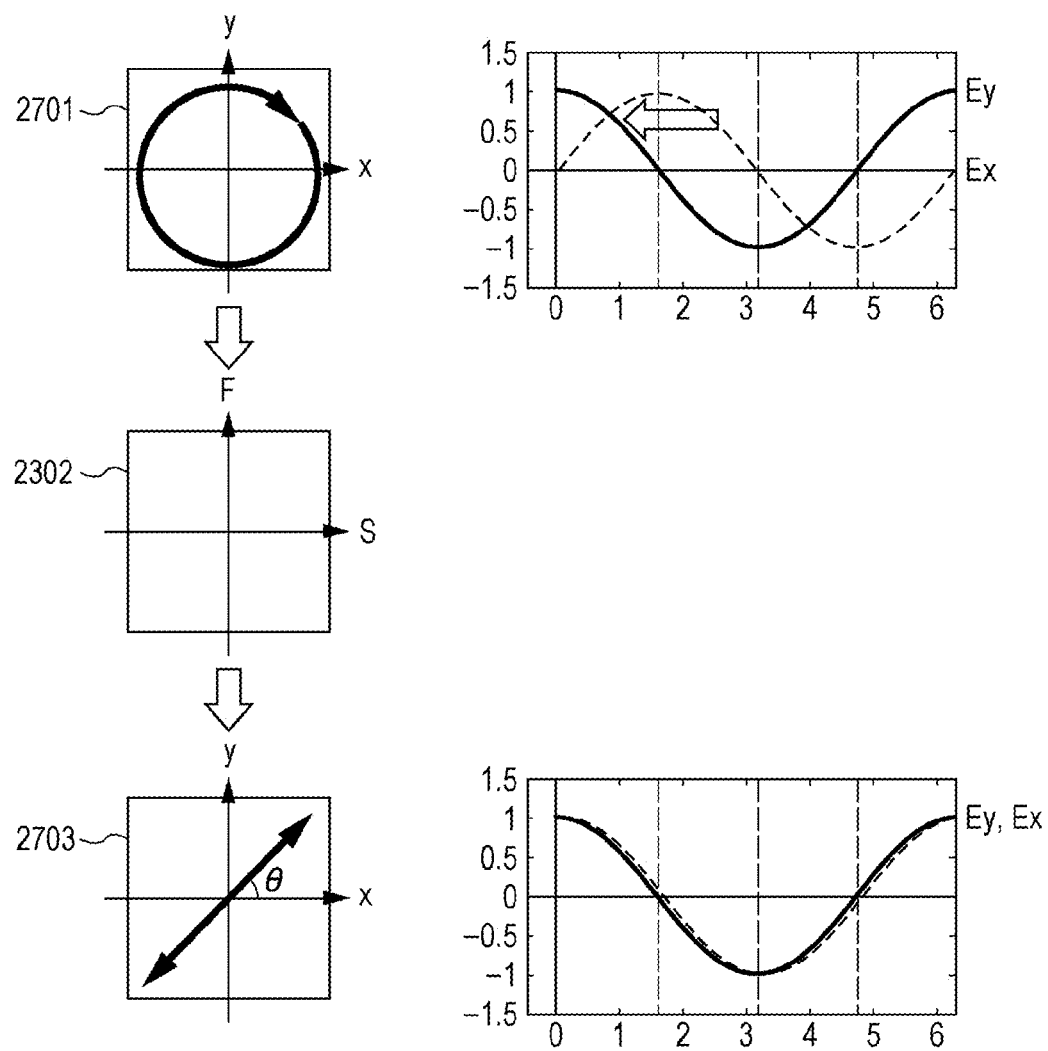
FIG. 27 illustrates the manner in which clockwise circularly polarized returning light is converted into linearly polarized light that is polarized in a direction of 45°.

FIGS. 27 and 28 illustrate the manner in which the returning light, which is the circularly polarized light, is converted into two types of linearly polarized light having orthogonal polarization directions. FIG. 27 illustrates the manner in which clockwise circularly polarized light 2701 passes through the variable retarder as the returning light while the variable retarder is set such that an X-axis is an S-axis (slow or delayed axis), a Y-axis is an F-axis (fast or advanced axis), and a phase shift is $\lambda/4$. In this case, the clockwise circularly polarized light 2701 is converted into linearly polarized light 2703 with a polarization angle of $\theta=45°$. FIG. 28 illustrates the manner in which the clockwise circularly polarized light 2701 passes through the variable retarder while the variable retarder is set such that the X-axis is the F-axis (fast or advanced axis), the Y-axis is the S-axis (slow or delayed axis), and the phase shift is $\lambda/4$. In this case, the clockwise circularly polarized light 2701 is converted into linearly polarized light 2803 with a polarization angle of $\theta=135°$.

Figure 29:
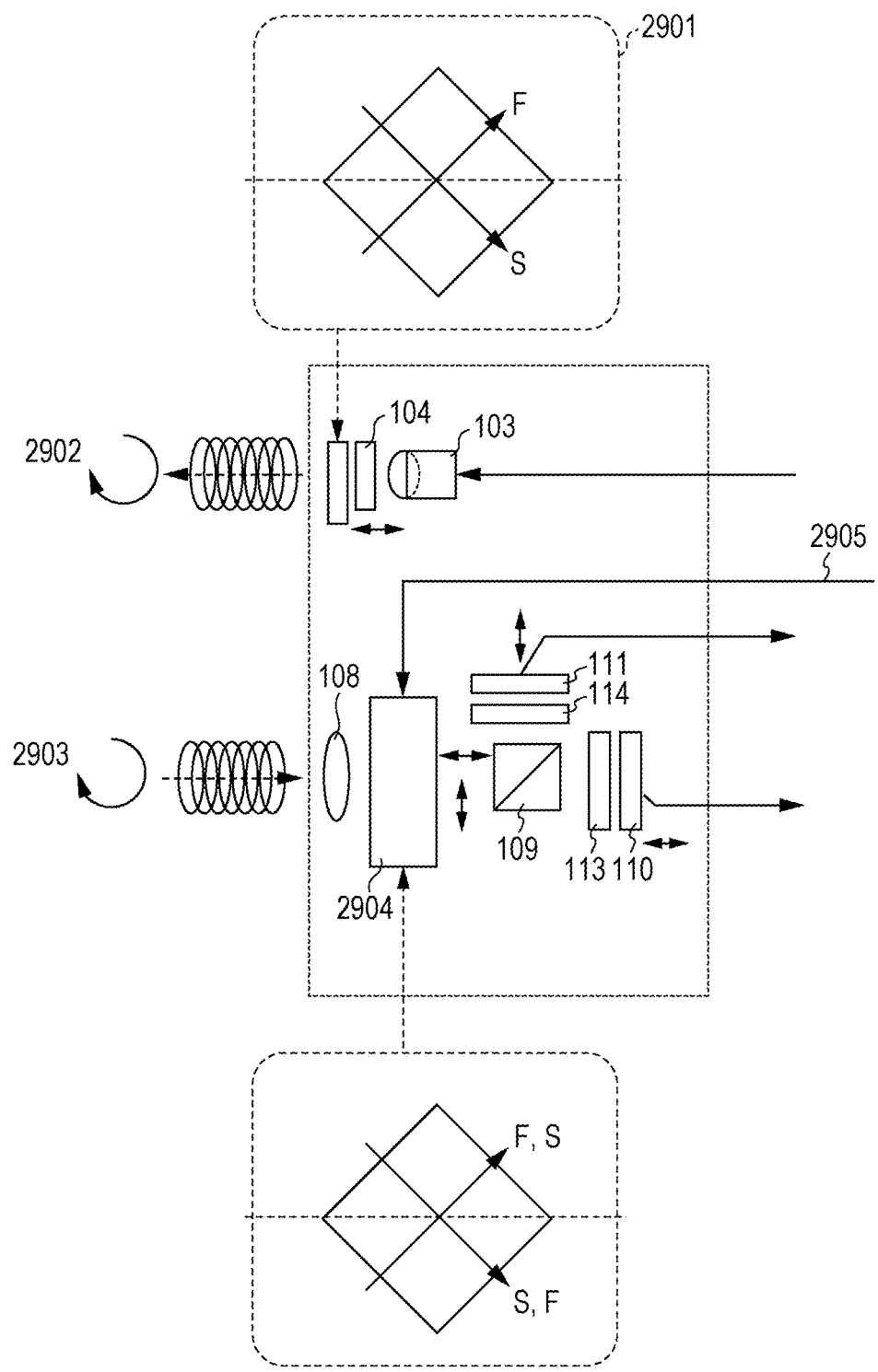
FIG. 29 illustrates the structure of an end portion of a polarization imaging apparatus according to the third embodiment pf the present disclosure.

FIG. 29 is a schematic diagram illustrating the structure of an end portion included in a polarization image processing apparatus according to a third embodiment of the present disclosure. The image processing apparatus serves as a flexible endoscope for inspection or a rigid endoscope for surgery. The overall structure of this apparatus is the same as that of the apparatus illustrated in FIG. 7. Therefore, only an end portion of an endoscope 101, which differs from that in the apparatus illustrated in FIG. 7, will be described. The illumination unit included in the end portion of the endoscope includes a $\lambda/4$ plate 2901, a polarizing plate 104, and a light source 103 arranged in that order from the object side. As shown in FIG. 29, the $\lambda/4$ plate 2901 is arranged at an angle of 45° with respect to the direction of the polarizing plate 104, so that an object is illuminated with clockwise circularly polarized illumination light 2902. Returning light that is reflected by the object is clockwise circularly polarized light 2903 in which the degree of polarization is reduced. The clockwise circularly polarized light 2903 passes through an objective lens 108 and is incident on a variable retarder 2904 that is at an angle of 45° with respect to polarizing filter axes at the imaging side. The state of the variable retarder 2904 can be alternately switched between two states in accordance with a voltage applied through a phase control line 2905. Accordingly, the clockwise circularly polarized light 2903 is alternately converted into two types of linearly polarized light having polarization angles of 0° and 90°. Each of the two types of linearly polarized light is divided into two light components by a beam splitter 109 along optical paths. The light components pass through the polarizing filters 114 and 113, and reach imaging devices 111 and 110, where polarization imaging is performed.

In the present embodiment, it is assumed that the illumination light is clockwise circularly polarized light. However, the illumination light may instead be counterclockwise circularly polarized light. In addition, the illumination light may be elliptically polarized light instead of circularly polarized light. In such a case, the variable retarder 2904 may shift the phase of light to be incident on the beam splitter 109 by an appropriate amount instead of $\lambda/4$. Thus, effects similar to those of the present embodiment can be obtained.

According to the embodiments of the present disclosure, irregularities on a surface of a smooth, transparent or translucent object can be appropriately detected, and can also be emphasized on a display such that the irregularities can be easily recognized by a human being. The embodiments may be appropriately applied to an inspection of irregularities that cannot be easily realized by brightness imaging. The embodiments may be employed in the fields of medical endoscopes required to observe translucent mucous membranes or medical cameras used for dermatological, dental, ophthalmological, or surgical treatment.

What is claimed is:

1. An image processing apparatus comprising:
    an illumination unit that illuminates an object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the image processing apparatus;
    a splitter that splits returning light that returns from the object into at least two returning light components;
    a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light;
    a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

2. The image processing apparatus according to claim 1, wherein the processing unit performs
a first process of taking an average of the first polarization image and the fourth polarization image to generate an average parallel-Nicols image,
a second process of taking an average of the second polarization image and the third polarization image to generate an average crossed-Nicols image, and
a third process of determining the difference by performing a subtraction between the average parallel-Nicols image and the average crossed-Nicols image.

3. The image processing apparatus according to claim 2, wherein the processing unit generates a brightness image by adding the first, second, third, and fourth polarization images.

4. The image processing apparatus according to claim 3, wherein the illumination unit includes a plurality of the first light sources that emit the first illumination light and a plurality of the second light sources that emit the second illumination light.

5. The image processing apparatus according to claim 4, comprising an endoscope including an end portion which includes the illumination unit, the splitter, and the first and second polarization imaging devices,
wherein the processing unit is connected to the endoscope.

6. The image processing apparatus according to claim 4, comprising an endoscope including an end portion which includes the illumination unit, a polarization camera unit that is disposed behind the end portion, and a relay lens that receives the returning light from the end portion and guides the returning light to the polarization camera unit,
wherein the polarization camera unit includes the splitter and the first and second polarization imaging devices, the splitter being arranged so as to receive the returning light guided by the relay lens, and
wherein the processing unit is connected to the endoscope.

7. The image processing apparatus according to claim 6, wherein the processing unit includes a groove-region detecting unit that detects a small groove in a surface of the object.

8. The image processing apparatus according to claim 7, wherein the processing unit includes an image combining unit which displays the small groove in the surface of the object in an emphasized manner.

9. The image processing apparatus according to claim 7, further comprising:
a minimization process unit that compares a brightness of a pixel of the second polarization image with a brightness of a pixel of the third polarization image corresponding to the pixel of the second polarization image, and selects the pixel having the lower brightness; and
an image selecting unit that generates a crossed-Nicols image in which halation is suppressed on the basis of the brightness of the pixel selected by the minimization process.

10. An image processing apparatus comprising:
an illumination unit that illuminates an object with first illumination light and second illumination light alternately, the first illumination light being polarized in a first direction and the second illumination light being polarized in a second direction that crosses the first direction, an illumination axis of the first illumination light and an illumination axis of the second illumination light substantially coinciding with an imaging axis of the image processing apparatus;
a splitter that splits returning light that returns from the object into first, second, and third light components;
a first polarization imaging device that receives the first light component, the first polarization imaging device obtaining a first polarization image polarized in the first direction while the object is being illuminated with the first illumination light and obtaining a second polarization image polarized in the first direction while the object is being illuminated with the second illumination light;
a second polarization imaging device that receives the second light component, the second polarization imaging device obtaining a third polarization image polarized in the second direction while the object is being illuminated with the first illumination light and obtaining a fourth polarization image polarized in the second direction while the object is being illuminated with the second illumination light;
a third polarization imaging device that receives the third light component, the third polarization imaging device obtaining a fifth polarization image polarized in a third direction, which differs from the first and second directions, while the object is being illuminated with the first illumination light and obtaining a sixth polarization image polarized in the third direction while the object is being illuminated with the second illumination light; and
a processing unit that receives the second, third, fifth, and sixth polarization images from the first, second, and third polarization imaging devices and detects a condition of the object on the basis of a difference between a sum of the fifth polarization image and the sixth polarization image and a sum of the second polarization image and the third polarization image.

11. The image processing apparatus according to claim 10,
wherein the first direction and the second direction are orthogonal to each other, and
wherein the third direction is at an angle in the range of 10 degrees or more and 60 degrees or less with respect to the first direction.

12. The image processing apparatus according to claim 11, wherein the processing unit performs
a first process of taking an average of the fifth polarization image and the sixth polarization image to generate an average oblique-Nicols image,
a second process of taking an average of the second polarization image and the third polarization image to generate an average crossed-Nicols image, and
a third process of determining the difference by performing a subtraction between the average oblique-Nicols image and the average crossed-Nicols image.

13. The image processing apparatus according to claim 12, wherein the processing unit generates a brightness image by adding the first, second, third, and fourth polarization images.

14. The image processing apparatus according to claim 13, wherein the illumination unit includes a plurality of the first light sources that emit the first illumination light and a plurality of the second light sources that emit the second illumination light.

15. The image processing apparatus according to claim 14, comprising an endoscope including an end portion which includes the illumination unit, the splitter, and the first and second polarization imaging devices,
wherein the processing unit is connected to the endoscope.

16. The image processing apparatus according to claim 14, comprising an endoscope including an end portion which includes the illumination unit, a polarization camera unit that is disposed behind the end portion, and a relay lens that receives the returning light from the end portion and guides the returning light to the polarization camera unit,
wherein the polarization camera unit includes the splitter and the first and second polarization imaging devices, the splitter being arranged so as to receive the returning light guided by the relay lens, and
wherein the processing unit is connected to the endoscope.

17. The image processing apparatus according to claim 16, wherein the processing unit includes a groove-region detecting unit that detects a small groove in a surface of the object.

18. The image processing apparatus according to claim 17, wherein the processing unit includes an image combining unit which displays the small groove in the surface of the object in an emphasized manner.

19. An image processing apparatus comprising:
an illumination unit that illuminates an object with first illumination light and second illumination light alternately, the first illumination light being in a first state of polarization and the second illumination light being in a second state of polarization that differs from the first state of polarization, an illumination axis of the first illumination light and an illumination axis of the second illumination light substantially coinciding with an imaging axis of the image processing apparatus;
a splitter that splits returning light that returns from the object into at least two returning light components;
a phase shift element arranged so as to allow the returning light that returns from the object to pass therethrough, the phase shift element converting clockwise polarized light into light polarized in a first direction and counterclockwise polarized light into light polarized in a second direction that is orthogonal to the first direction;
a first polarization imaging device that receives one of the at least two returning light components, the first polarization imaging device obtaining a first polarization image polarized in the first direction while the object is being illuminated with the first illumination light and obtaining a second polarization image polarized in the first direction while the object is being illuminated with the second illumination light;
a second polarization imaging device that receives another one of the at least two returning light components, the second polarization imaging device obtaining a third polarization image polarized in the second direction while the object is being illuminated with the first illumination light and obtaining a fourth polarization image polarized in the second direction while the object is being illuminated with the second illumination light; and
a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

20. The image processing apparatus according to claim 19, wherein one of the first state of polarization and the second state of polarization is clockwise circular or elliptical polarization, and the other one of the first state of polarization and the second state of polarization is counterclockwise circular or elliptical polarization.

21. The image processing apparatus according to claim 20, wherein the phase shift element is a quarter wave plate.

22. An image processing apparatus comprising:
an illumination unit that illuminates an object with circularly polarized light or elliptically polarized light, an illumination axis of the illuminated light substantially coinciding with an imaging axis of the image processing apparatus;
a splitter that splits returning light that returns from the object into at least two returning light components;
a variable phase shift element arranged so as to allow the returning light that returns from the object to pass therethrough, the variable phase shift element operating in a first mode and a second mode alternately, the returning light being converted into light in a first state of polarization that is polarized in a first direction in the first mode and being converted into light in a second state of polarization that is polarized in a second direction in the second mode, the second direction being orthogonal to the first direction;
a first polarization imaging device that receives one of the at least two returning light components, the first polarization imaging device obtaining a first polarization image polarized in the first direction while the variable phase shift element is operating in the first mode and obtaining a second polarization image polarized in the first direction while the variable phase shift element is operating in the second mode;
a second polarization imaging device that receives another one of the at least two returning light components, the second polarization imaging device obtaining a third polarization image polarized in the second direction while the variable phase shift element is operating in the first mode and obtaining a fourth polarization image polarized in the second direction while the variable phase shift element is operating in the second mode; and
a processing unit that receives the first, second, third, and fourth polarization images from the first and second polarization imaging devices and detects a condition of the object on the basis of a difference between a sum of the first polarization image and the fourth polarization image and a sum of the second polarization image and the third polarization image.

* * * * *